US012685511B2

(12) United States Patent     (10) Patent No.: US 12,685,511 B2

Hammond et al.     (45) Date of Patent:    Jul. 21, 2026

(54) ULTRASOUND WITH SIMULTANEOUS TRANSDUCER ARRAYS

(71) Applicant: FUJIFILM SonoSite, Inc., Bothell, WA (US)

(72) Inventors: Ryan Hammond, Tacoma, WA (US); Brittney Klingenberg, Bothell, WA (US); Jean Tsou, Seattle, WA (US); Lillian Larson, Kirkland, WA (US); David Knapp, Bellevue, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 0 days.

(21) Appl. No.: 18/975,800

(22) Filed: Dec. 10, 2024

(65) Prior Publication Data

US 2026/0157728 A1    Jun. 11, 2026

(51) Int. Cl.
   *A61B 8/00*      (2006.01)
   *A61B 8/08*      (2006.01)

(52) U.S. Cl.
   CPC ............ *A61B 8/463* (2013.01); *A61B 8/0841* (2013.01); *A61B 8/4488* (2013.01); *A61B 8/4494* (2013.01); *A61B 8/488* (2013.01)

(58) Field of Classification Search
   CPC ..... A61B 8/463; A61B 8/0841; A61B 8/4488; A61B 8/4494; A61B 8/488
   See application file for complete search history.

(56) References Cited

U.S. PATENT DOCUMENTS

| | | | | |
|---|---|---|---|---|
| 4,566,459 A | * | 1/1986 | Umemura | ........... G01S 7/52046 |
| | | | | 600/443 |
| 4,733,562 A | * | 3/1988 | Saugeon | ............... G01S 7/5206 |
| | | | | 73/628 |
| 5,113,706 A | * | 5/1992 | Pittaro | ................. G01N 29/449 |
| | | | | 600/447 |
| 5,143,075 A | * | 9/1992 | Ishizuka | ............. G01S 15/8918 |
| | | | | 600/447 |
| 5,846,201 A | * | 12/1998 | Adams | ..................... A61B 8/14 |
| | | | | 600/447 |
| 6,014,897 A | * | 1/2000 | Mo | ...................... G01S 7/52047 |
| | | | | 73/628 |

(Continued)

FOREIGN PATENT DOCUMENTS

CN      102809610 A   *   12/2012

*Primary Examiner* — Oommen Jacob
(74) *Attorney, Agent, or Firm* — Colby Nipper PLLC

(57)      ABSTRACT

Systems and methods for ultrasound devices with simultaneous arrays are disclosed. These systems and methods include an ultrasound having simultaneous arrays that can be used during an examination of an anatomy. The simultaneous arrays include at least a first array and a second array, where the first array transmits first ultrasound signals focused at a first depth and the second array transmits second ultrasound signals focused at a second depth that differs from the first depth. A first image is generated based on reflected signals of the first ultrasound signals from the anatomy and a second image is generated based on reflected signals of the second ultrasound signals from the anatomy. The first image can be first displayed, and the system can automatically replace the first image with the second image when an interventional instrument, shown in the first image, reaches a threshold depth of a region of interest.

20 Claims, 16 Drawing Sheets

(56)  References Cited

U.S. PATENT DOCUMENTS

| | | | | | |
|---|---|---|---|---|---|
| 6,108,572 | A * | 8/2000 | Panda | ................. | G01S 7/52039 |
| | | | | | 600/407 |
| 6,146,330 | A * | 11/2000 | Tujino | ................ | G01S 7/52038 |
| | | | | | 600/458 |
| 8,758,248 | B2 * | 6/2014 | Lin | .................... | G01S 7/52046 |
| | | | | | 73/645 |
| 9,177,543 | B2 * | 11/2015 | Vitek | .................... | B06B 1/0633 |
| 10,674,995 | B2 * | 6/2020 | Pelissier | .............. | A61B 8/5269 |
| 10,786,224 | B2 * | 9/2020 | Grim | .................. | A61B 17/3403 |
| 12,016,732 | B2 * | 6/2024 | Matsumoto | .......... | A61B 8/4488 |
| 2001/0020131 | A1 * | 9/2001 | Kawagishi | .......... | G10K 11/346 |
| | | | | | 600/443 |
| 2003/0025721 | A1 * | 2/2003 | Clapper | ................ | G06F 3/0354 |
| | | | | | 715/700 |
| 2009/0076392 | A1 * | 3/2009 | Oshiki | ................ | G01S 15/8927 |
| | | | | | 600/459 |

| | | | | | |
|---|---|---|---|---|---|
| 2012/0197133 | A1 * | 8/2012 | McKenna | ............ | A61B 5/0261 |
| | | | | | 600/476 |
| 2013/0041252 | A1 * | 2/2013 | Vignon | ................ | A61B 8/0841 |
| | | | | | 600/443 |
| 2013/0324989 | A1 * | 12/2013 | Leung | .................. | A61B 8/0841 |
| | | | | | 606/24 |
| 2014/0257110 | A1 * | 9/2014 | Chang | ................ | A61B 17/3403 |
| | | | | | 600/461 |
| 2016/0000399 | A1 * | 1/2016 | Halmann | .......... | A61B 17/3403 |
| | | | | | 600/461 |
| 2016/0015361 | A1 * | 1/2016 | Osawa | ................. | A61B 8/4444 |
| | | | | | 600/472 |
| 2016/0235485 | A1 * | 8/2016 | Belohlavek | ............ | A61M 5/158 |
| 2017/0014098 | A1 * | 1/2017 | Shao | ..................... | A61B 8/461 |
| 2017/0209124 | A1 * | 7/2017 | Gawazawa | .......... | A61B 8/0841 |
| 2020/0037984 | A1 * | 2/2020 | Poland | ................... | A61B 8/463 |
| 2020/0178927 | A1 * | 6/2020 | Patton | ................. | A61B 8/0841 |
| 2020/0390416 | A1 * | 12/2020 | Swan | ................... | A61B 8/5223 |
| 2021/0177373 | A1 * | 6/2021 | Xie | ........................ | G16H 50/30 |

* cited by examiner

100

200

Scanner
104

208

222

214

204

104-1

104-2

104-3

224

202

226

212

210

206

228

Y

Z

X

Ultrasound Machine
102

Display Device
108

System Electronics
216

Ultrasound Control
Subsystem
218

Ultrasound Imaging
Subsystem
220

Memory
110

User Interface 602-1

604

606

608

Superficial Image

610

User Interface 602-2

612

606

Deep Image

Deep
Image

Superficial
Image 800-1

800-2

800-3

1100

1400

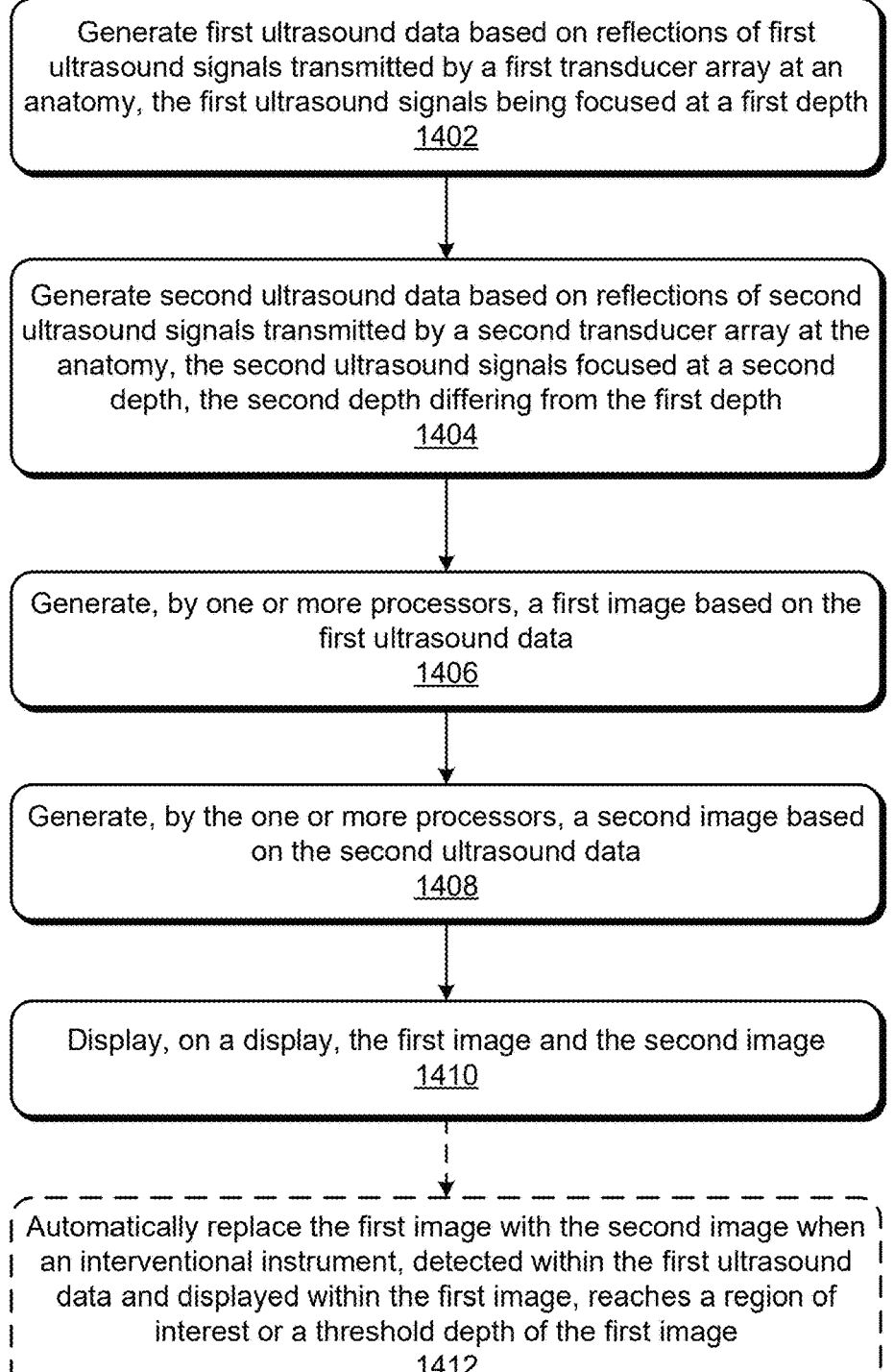

Generate first ultrasound data based on reflections of first ultrasound signals transmitted by a first transducer array at an anatomy, the first ultrasound signals being focused at a first depth
1402

Generate second ultrasound data based on reflections of second ultrasound signals transmitted by a second transducer array at the anatomy, the second ultrasound signals focused at a second depth, the second depth differing from the first depth
1404

Generate, by one or more processors, a first image based on the first ultrasound data
1406

Generate, by the one or more processors, a second image based on the second ultrasound data
1408

Display, on a display, the first image and the second image
1410

Automatically replace the first image with the second image when an interventional instrument, detected within the first ultrasound data and displayed within the first image, reaches a region of interest or a threshold depth of the first image
1412

FIG. 14

ULTRASOUND WITH SIMULTANEOUS TRANSDUCER ARRAYS

BACKGROUND

Ultrasound devices (e.g., scanners, probes, arrays, etc.) and ultrasound systems that utilize various ultrasound devices can generate ultrasound images by transmitting sound waves at frequencies above the audible spectrum (e.g., ultrasound signals) into a body, receiving echo signals (e.g., reflected signals) caused by the sound waves reflecting from internal body parts, and converting the echo signals into electrical signals for image generation. Ultrasound (e.g., diagnostic ultrasound, sonography, diagnostic medical sonography) is an imaging process that uses sound waves to produce images of structures inside a subject's body. Because they are non-invasive and non-ionizing, ultrasound is used ubiquitously.

In some cases, an examination may need superficial images and deep images of the subject's anatomy, which may necessitate a first examination using a first ultrasound transducer via a first ultrasound device (e.g., a probe, a scanner, etc.) configured to produce superficial images and a second examination using a second ultrasound transducer via a second ultrasound device configured to produce deep images. The utilization of two ultrasound devices can increase the length of the overall examination of the patient. Because the ultrasound examinations are completed sequentially, the ultrasound images are not generated synchronously with each other. Further, the two separate ultrasound examinations can produce two ultrasound images having different viewpoints since two separate ultrasound devices are used during the two distinct ultrasound examinations as the ultrasound devices can be misaligned due to the separate ultrasound examinations. Each of these aspects can lead to difficulty in interpreting the ultrasound images by medical personnel and may prevent the patient from receiving the best care possible.

SUMMARY

Systems, devices, and methods for ultrasound with simultaneous transducer arrays are disclosed. These systems and methods include an ultrasound system having simultaneous arrays that can be used during an examination of an anatomy. The simultaneous arrays include at least a first array and a second array, where the first transducer array is configured to transmit first ultrasound signals focused at a first depth and the second transducer array is configured to transmit second ultrasound signals focused at a second depth that differs from the first depth. A first ultrasound image can be generated based on reflected signals of the first ultrasound signals from the anatomy and a second ultrasound image can be generated based on reflected signals of the second ultrasound signals from the anatomy. The first ultrasound image can be first displayed by a display of the ultrasound system and the ultrasound system can be configured to automatically replace the first ultrasound image with the second ultrasound image when an interventional instrument, shown in the first ultrasound image, reaches a threshold depth or region of interest (ROI).

In some aspects, an ultrasound device is disclosed. The ultrasound device includes a multi-array ultrasound scanner configured to generate ultrasound data based on reflections of ultrasound signals transmitted by the multi-array ultrasound scanner at an anatomy. The multi-array ultrasound scanner includes at least a first transducer array and a second transducer array. The multi-array ultrasound scanner is configured to generate first ultrasound data based on reflections of first ultrasound signals transmitted by the first transducer array at the anatomy and second ultrasound data based on reflections of second ultrasound signals transmitted by the second transducer array at the anatomy. The first ultrasound signals are focused at a first depth and the second ultrasound signals are focused at a second depth. The ultrasound device includes one or more processors configured to generate a first image based on the first ultrasound data and generate a second image based on the second ultrasound data. The ultrasound device includes a device configured to display the first image and the second image.

In some aspects, a method for a multi-array ultrasound scanner having a first transducer array and a second transducer array is disclosed. The method includes generating first ultrasound data based on reflections of first ultrasound signals transmitted by the first transducer array at an anatomy, the first ultrasound signals being focused at a first depth. The method includes generating ultrasound data based on reflections of second ultrasound signals transmitted by the second transducer array at the anatomy, the second ultrasound signals being focused at a second depth that differs from the first depth. The method includes generating, by one or more processors, a first image based on the first ultrasound data and generating, by the one or more processors, a second image based on the second ultrasound data. The method includes displaying, on a display, the first image and the second image.

In some aspects, an ultrasound system is disclosed. The ultrasound system includes a multi-array ultrasound scanner configured to generate ultrasound data based on reflections of ultrasound signals transmitted by the multi-array ultrasound scanner at an anatomy. The multi-array ultrasound scanner includes at least a first transducer array and a second transducer array. The multi-array ultrasound scanner is configured to generate first ultrasound data based on reflections of first ultrasound signals transmitted by the first transducer array at the anatomy and second ultrasound data based on reflections of second ultrasound signals transmitted by the second transducer array at the anatomy. The first ultrasound signals are focused at a first depth and the second ultrasound signals are focused at a second depth. The ultrasound system includes one or more processors configured to generate a first image based on the first ultrasound data and generate a second image based on the second ultrasound data. The second image is generated responsive to an interventional instrument, detected within the first ultrasound data, reaching a threshold depth or ROI. The ultrasound system includes a display configured to display the first image and the second image.

BRIEF DESCRIPTION OF THE DRAWINGS

The appended drawings illustrate examples and are, therefore, exemplary embodiments and not considered to be limiting in scope. Throughout the drawings, the same numbers are used to reference like features and components.

FIG. 2 illustrates an example implementation of the ultrasound system illustrated in the environment of FIG. 1.

FIG. 8-1 illustrates an example ultrasound system with simultaneous transducer arrays.

FIG. 8-2 illustrates an example ultrasound system with simultaneous transducer arrays.

FIG. 8-3 illustrates an example ultrasound system with simultaneous transducer arrays.

FIG. 14 depicts a method for a multi-array ultrasound scanner having simultaneous transducer arrays.

DETAILED DESCRIPTION

Figure 1:
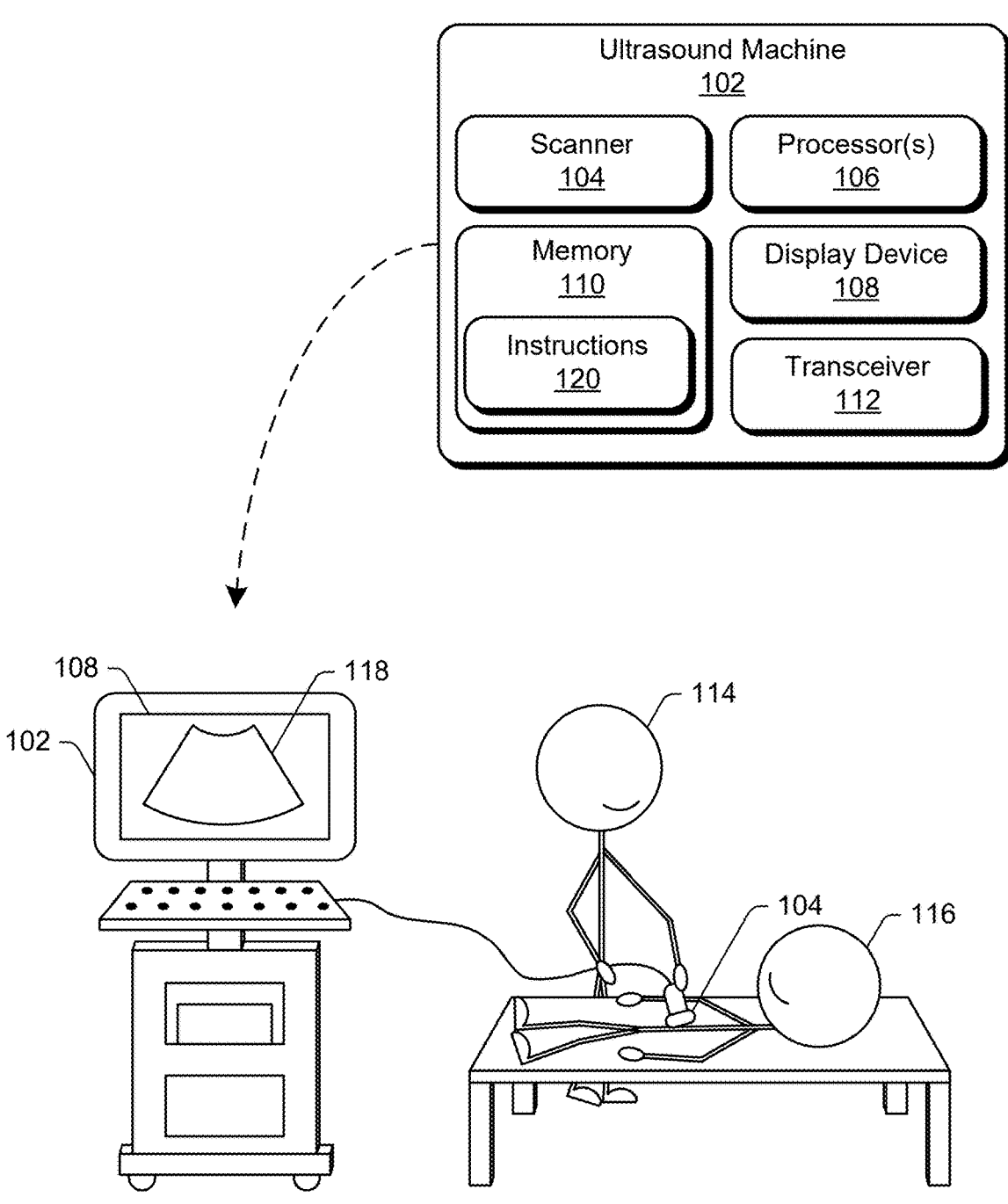
FIG. 1 illustrates an ultrasound system in an environment for an ultrasound examination with simultaneous transducer arrays.

Disclosed herein are systems and methods for an ultrasound device or system that uses a multi-array scanner having simultaneous transducer arrays. In one aspect, simultaneous transducer arrays can indicate that the transducer arrays are transmitting and receiving at a same time. In another aspect, simultaneous transducer arrays can indicate that the transducer arrays are interleaved in time so an overall perception of a user is that the transducer arrays are transmitting and receiving at a same time. Ultrasound images are generated by transmitting sound waves at frequencies above the audible spectrum (e.g., ultrasound signals) into a body, receiving echo signals (e.g., reflected signals) caused by the sound waves reflecting from internal body parts and/or an interventional instrument, and converting the echo signals into electrical signals for image generation. In some cases, an ultrasound examination of an anatomy may need both superficial images and deep images, which can necessitate a first examination using a first ultrasound transducer to produce superficial images. The additional need for deep images can cause a second examination using a second ultrasound transducer, which can increase the time for the overall examination, which may prevent providing the best possible care to a patient. The ultrasound images provided by the two separate ultrasound examinations (e.g., scanning sessions) may not be co-registered (e.g., scanned in the same plane). Additionally, the two ultrasound images are not generated synchronously with each other due to the two separate ultrasound examinations. Viewing ultrasound images that have different viewpoints and are not generated synchronously can hamper the interpretation of the ultrasound images by the care provider.

While performing the two separate ultrasound examinations potentially needed to properly scan a specific area of an anatomy, the care provider may need to focus at least some attention on the specific properties of the transducer array used to scan the anatomy, as well as try to ensure that both examinations are taken from the same viewpoint. As the examinations are done separately, the care provider may not be able to use the first generated ultrasound image while performing the second examination as the first ultrasound image is not a live image. Further, the care provider cannot use both a superficial image and a deep image to aid in the insertion of an interventional instrument into an anatomy as both images cannot be live due to the two separate examinations needed to provide both such images.

To this end, the present disclosure describes devices, systems, and techniques directed at using an ultrasound with simultaneous transducer arrays. The present disclosure describes ultrasound with simultaneous transducer arrays. An ultrasound simultaneous transducer array (e.g., a multi-array scanner) includes at least a first ultrasound transducer array and a second ultrasound transducer array. The first ultrasound transducer array can be configured to transmit first ultrasound signals having a first frequency and receive ultrasound signals of the first ultrasound signals reflected from a portion of an anatomy. Likewise, the second ultrasound transducer array can be configured to transmit second ultrasound signals having a second frequency and receive ultrasound signals of the second ultrasound signals reflected from a portion of the anatomy. The first ultrasound signals can be focused at a first depth and the second ultrasound signals can be focused at a second depth. In this way, two ultrasound images can be produced of an anatomy having different properties. For example, one ultrasound image can be a superficial image of a first depth (e.g., less than ten (10) centimeters) into the anatomy and the other ultrasound image can be a deep image of a second depth (e.g., less than thirty (30) centimeters). A caregiver may be able to use both images simultaneously to better interpret the ultrasound images to understand the internal structures of the anatomy. Further, the caregiver may be able to use both ultrasound images simultaneously to guide the insertion of an interventional instrument to an ROI within the anatomy.

In some aspects, the ultrasound system can be configured to display a first ultrasound image (e.g., a superficial ultrasound image) as an interventional instrument is inserted into the anatomy. The ultrasound system can be configured to automatically display a second ultrasound image (e.g., a deep ultrasound image) when the interventional instrument reaches a threshold depth. The ultrasound system can be configured to automatically replace the first ultrasound image with the second ultrasound image upon the interventional instrument reaching the threshold depth or upon the interventional instrument nearing the threshold depth. Alternatively, the ultrasound system can be configured to display the second ultrasound image along with the first ultrasound image upon the interventional instrument reaching the threshold depth or upon the interventional instrument nearing the threshold depth. The threshold depth can be selectable by a user. Alternatively, the ultrasound system can be configured to automatically determine the threshold depth. For example, a machine-learned model can determine the threshold depth based on an area of the anatomy that is being examined. The ultrasound system can be configured to display an ROI. The ROI can be selected by a user or the ROI can be displayed automatically based on a determination from a machine-learned model. For example, the machine-learned model can determine an ROI based on a depth selected by a user.

In other aspects, the ultrasound system can be configured to provide a user interface that can be used to control various aspects of the ultrasound system with simultaneous transducer arrays. For example, the user interface can enable the selection of the gain and/or depth of one or both transducer arrays of the simultaneous transducer arrays. The user interface can enable the selection of preset examinations, which automatically determines the operation of the simultaneous transducer arrays. The user interface can enable the selection of a type of ultrasound image to be captured. For example, a user may be able to select a superficial ultrasound image (e.g., having a depth of less than ten (10) centimeters), a deep ultrasound image (e.g., having a depth of less than thirty (30) centimeters), or a fused ultrasound image. A fused ultrasound image can be a combination of a superficial ultrasound image and a deep ultrasound image. For example, a fused ultrasound image can overlay a deep ultrasound image on a superficial ultrasound image. In one aspect, a portion of the deep ultrasound image can overlap with a portion of the deep ultrasound image. A fused image can enable a caregiver to provide better care to a patient.

The following discussion describes environments, techniques that can be employed in the environments, and example methods. Although techniques and apparatuses for ultrasound with simultaneous transducer arrays are described, it is to be understood that the subject of the appended claims is not necessarily limited to the specific features or methods described. Rather, the specific features and methods are disclosed as example implementations and reference is made to the environment by way of example only.

Example Ultrasound System

FIG. 1 illustrates an ultrasound system in an environment for an ultrasound examination with simultaneous transducer arrays. An ultrasound system 100 in FIG. 1 includes an ultrasound machine 102 and an ultrasound scanner 104. The ultrasound machine 102 generates high-frequency sound waves (e.g., ultrasound signals) that are transmitted from the ultrasound scanner 104. The ultrasound scanner 104 can include simultaneous transducer arrays as disclosed herein. In some implementations, the scanner 104 is an ultrasound scanner, which can also be referred to as an ultrasound probe or ultrasound transducer. The ultrasound machine 102 generates imaging data based on the ultrasound signals reflecting off a patient's anatomy (e.g., body structure). The ultrasound machine 102 also can generate imaging data based on the ultrasound signals reflecting off an interventional instrument that has been inserted into the patient's body. The ultrasound machine 102 includes various components, some of which include the scanner 104, one or more processors 106, a display device 108, a memory 110, and a transceiver 112.

A user 114 (e.g., nurse, ultrasound technician, operator, sonographer, clinician, etc.) directs the scanner 104 having simultaneous transducer arrays toward a patient 116 to non-invasively scan internal bodily structures (e.g., patient anatomies such as organs, tissues, bones, etc.) of the patient 116 as well as an interventional instrument (e.g., needle) for testing, diagnostic, therapeutic, or procedural reasons. In some implementations, the scanner 104 includes simultaneous ultrasound transducer arrays and electronics communicatively coupled to the simultaneous ultrasound transducer arrays to simultaneously transmit at least two different ultrasound signals to the patient's 116 anatomy and receive ultrasound signals reflected from the patient's 116 anatomy and/or from the interventional instrument.

In embodiments, the scanner 104 is configured to transmit ultrasound signals and receive ultrasound signals reflected off the patient's 116 anatomy and/or the interventional instrument within the patient's 116 anatomy. In embodiments, the scanner 104 is a multi-array scanner. For instance, a multi-array scanner in accordance with the present disclosure can include one or more of the arrays described in U.S. patent application Ser. No. 18/613,694 filed on Mar. 22, 2024, entitled Multi-Dimensional and Multi-Frequency Ultrasound Transducers to Zhang et al., the disclosure of which is incorporated herein by reference in its entirety. A multi-array scanner in accordance with the present invention can include one or more of the arrays described in U.S. patent application Ser. No. 17/561,313 filed on Dec. 23, 2021, entitled Array Architecture and Interconnection for Transducers to Li et al., the disclosure of which is incorporated herein by reference in its entirety.

The system 100 includes a display device 108 coupled to the one or more processors 106, which can include any suitable processor, number of processors, or processor system, such as one or more central processing units (CPUs), graphics processing units (GPUs), vector processors, reduced instruction set computer (RISC) processors, complex instruction set computer (CISC) processors, very long instruction word (VLIW) processors, etc. The processor 106 can execute instructions 120 stored on the memory 110 to perform operations disclosed herein for performing an ultrasound with simultaneous transducer arrays. For example, the processor 106 can process the reflected ultrasound signals to generate ultrasound data, including an ultrasound image. The display device 108 can be configured to generate and display an ultrasound image (e.g., ultrasound image 118) of the anatomy and/or an interventional instrument 606 based on the ultrasound data generated by the processor 106 from the reflected ultrasound signals detected by the scanner 104. In some aspects, the ultrasound data includes the ultrasound image 118 or data representing the ultrasound image 118. The transceiver 112 can be configured to transmit (e.g., over a network maintained by a care facility) the ultrasound data and/or any data related to the ultrasound examination, such as medical worksheet data, etc., to a medical archiver (e.g., a vendor neutral archive (VNA)). In embodiments, the transceiver 112 can receive data from the medical archiver, such as patient history data or previous examination data. Further, multi-array ultrasound scanners using simultaneous transducer arrays are discussed below in more detail with respect to FIGS. 2 and 3.

In some embodiments, the ultrasound scanner 104 is coupled to the ultrasound machine 102 via a communications module (not shown). In some implementations, the communications module includes a wireless coupling so that the scanner 104 is wirelessly coupled to the ultrasound machine 102 and communicates with the ultrasound machine 102 via one or more wireless transmitters, receivers, or transceivers over a wireless connection or network (e.g., Bluetooth™, Wi-Fi™, etc.). Additionally, or alternatively, one or more cables can connect the ultrasound scanner 104 to the ultrasound machine 102. The ultrasound machine 102 can provide transmit waveforms (or definitions thereof) to generate ultrasound to the ultrasound scanner 104 via the communications module, and/or the ultrasound scanner 104 can provide ultrasound data to the ultrasound machine 102 wirelessly or via one or more wires.

Example Ultrasound System

Figures 1, 8:
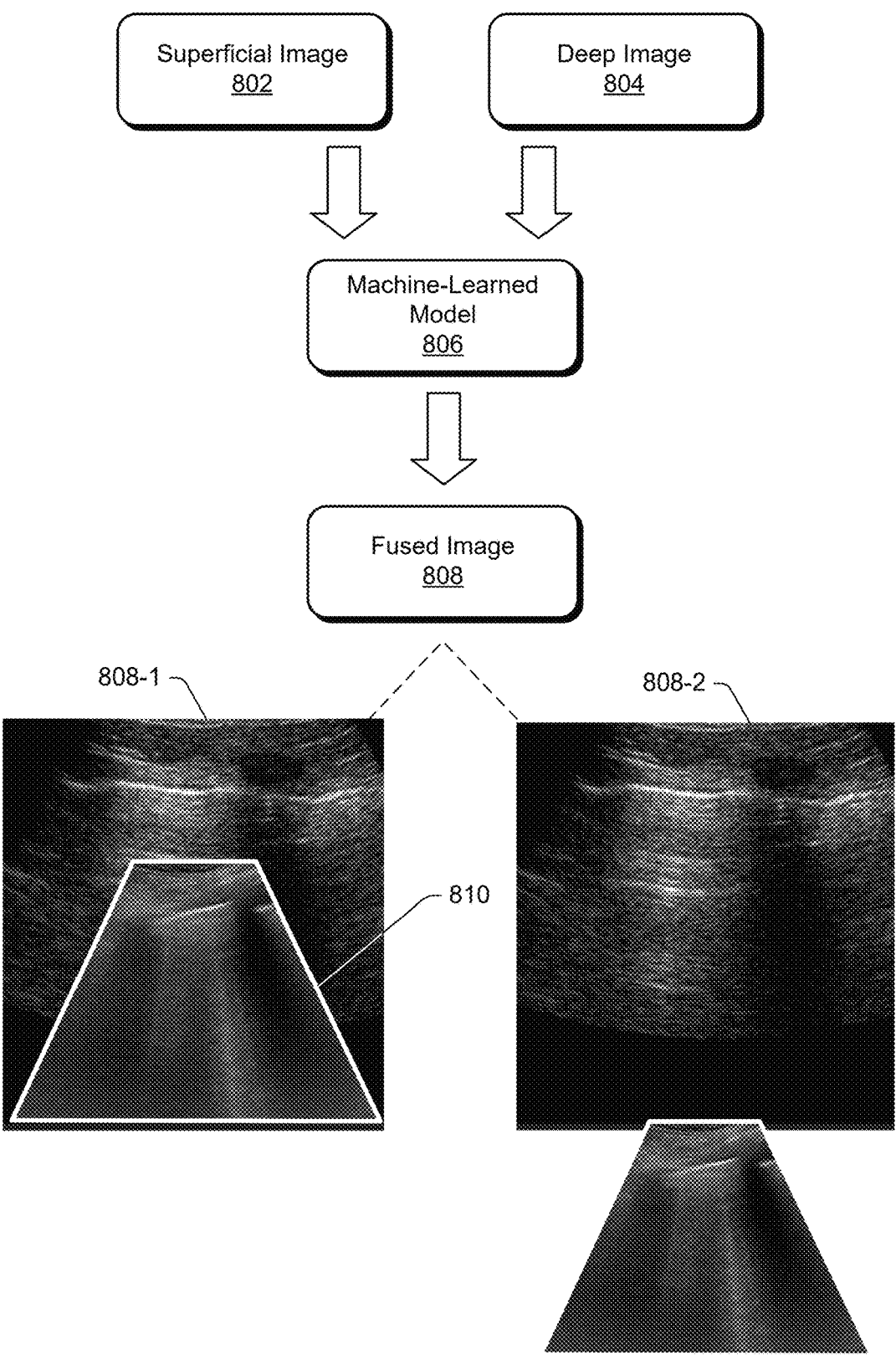
Figures 2, 8:
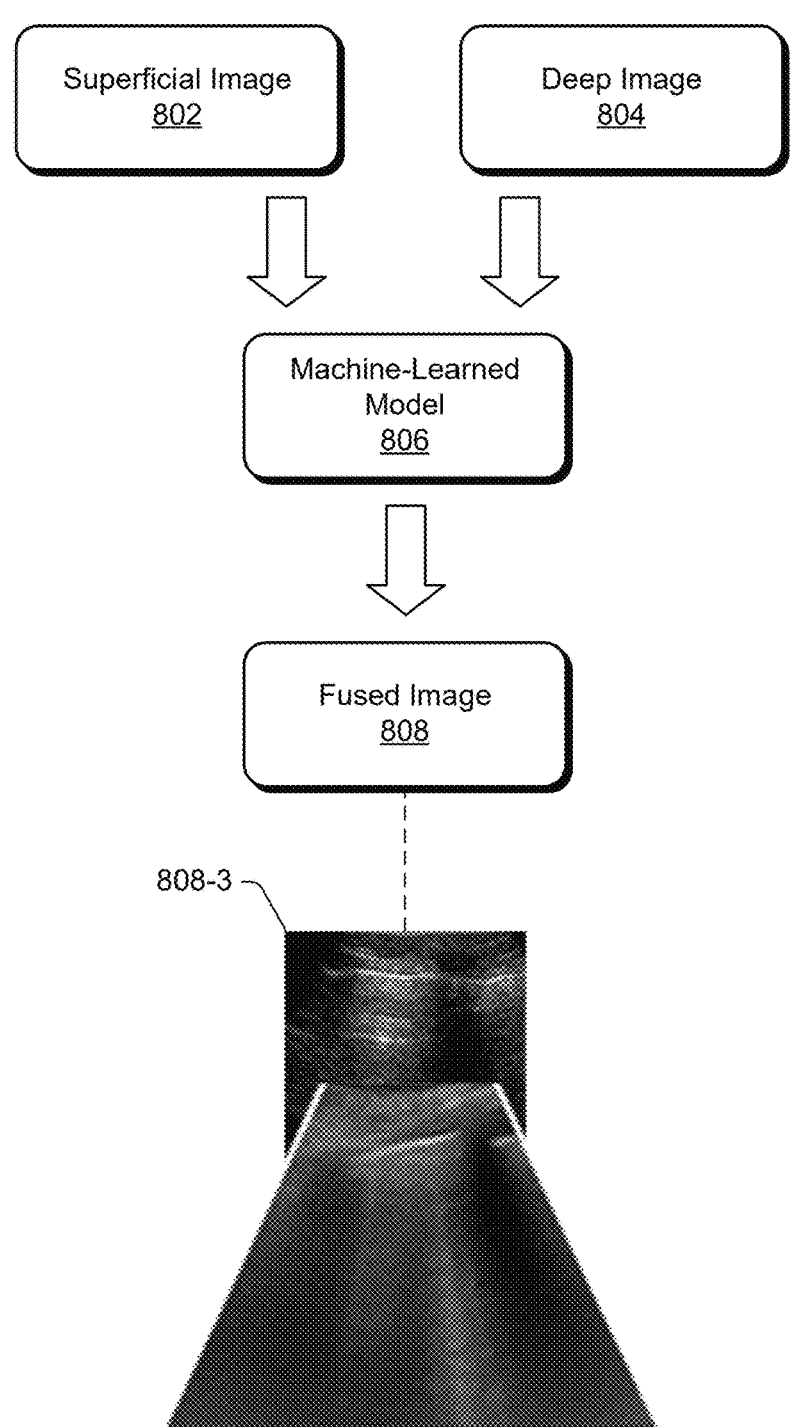
Figures 3, 8:
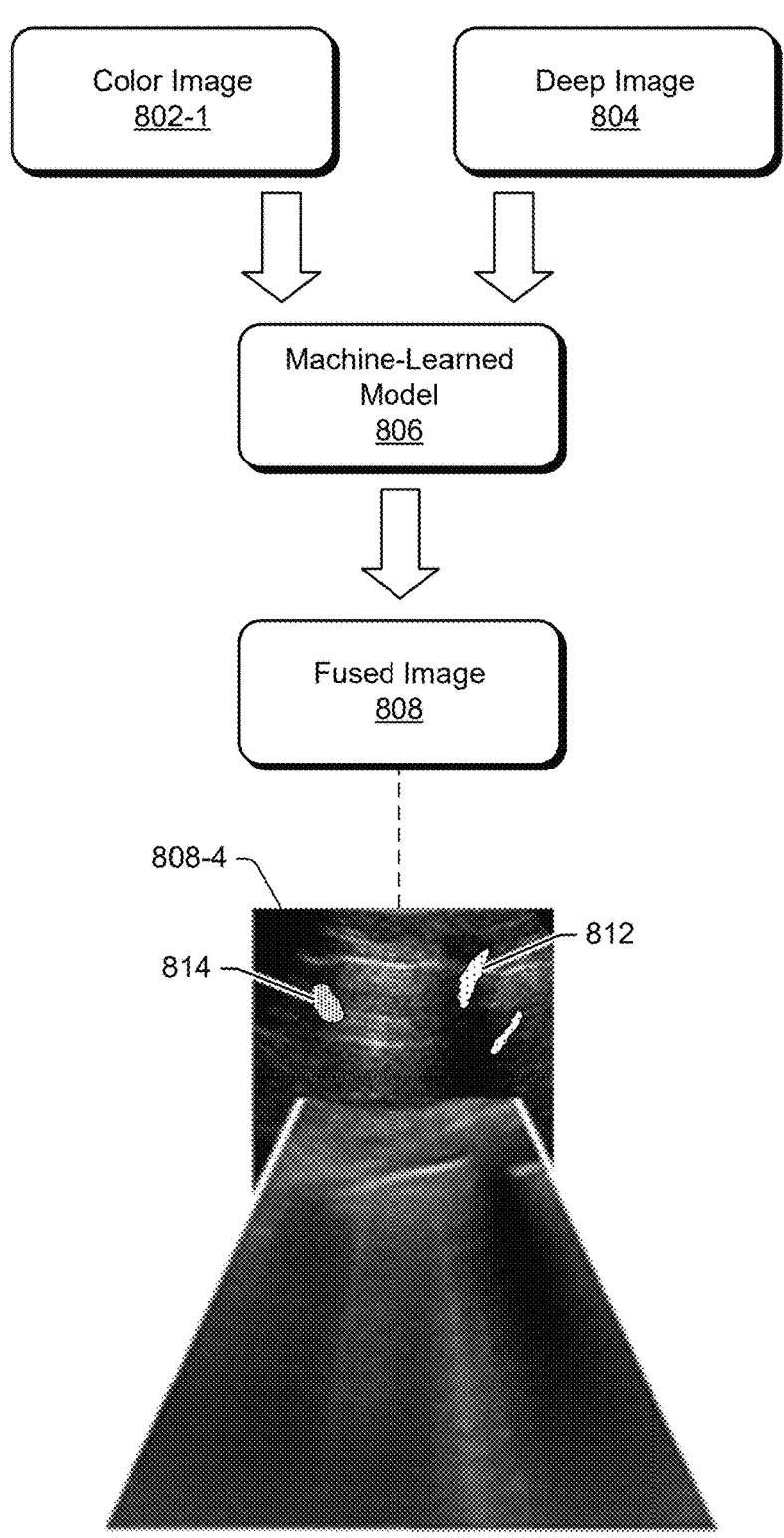

FIG. 2 illustrates an example implementation 200 of the ultrasound system 100 of FIG. 1. In the implementation, the scanner 104 (e.g., ultrasound scanner) can be any suitable type of ultrasound scanner. For example, the scanner 104 can be scanner 104-1 that is configured for handheld operation, for example, external to a patient's body. In another example, the scanner 104 includes a wearable scanner (e.g., wearable scanners 104-2 and 104-3) that include wearable patches (e.g., a patient-worn patch) that are configured to be placed on a patient's skin, such as for long-term monitoring. For instance, a wearable scanner in accordance with the present invention can include one or more of the scanners described in U.S. patent application Ser. No. 18/957,403 filed on Nov. 22, 2024, and entitled Determining Port Health with Ultrasound Transducers to Chamberlain et al., the disclosure of which is incorporated herein by reference in its entirety.

An ultrasound scanner, such as the ultrasound scanner 104, for an ultrasound device with simultaneous transducer arrays in accordance with the disclosed techniques can include a multi-array scanner (e.g., a multi-array transducer). A multi-array scanner in accordance with the disclosed techniques can include multi-array transducer assemblies having any combination of piezoelectric micromachined ultrasonic transducer (PMUT) array elements, lead zirconate titanate (PZT) array elements, and capacitive micromachined ultrasonic transducer (CMUT) array elements. In embodiments, a multi-array scanner that provides an ultrasound with simultaneous arrays can include a first array with array elements selected from the group consisting of PZT, PMUT, and CMUT array elements and a second array with additional array elements selected from the group consisting of PZT, PMUT, and CMUT array elements. The elements of the first array can be of a different type than the elements of the second array (e.g., the first array can include PMUT or PZT elements, and the second array can include CMUT elements). Alternatively, the elements of the first array can be of a same type as the elements of the second array (e.g., the first array and the second array can include PZT elements). The PMUT, CMUT, and/or PZT array elements can be tuned differently to enhance the performance (e.g., by using different tuning inductors or complex impedances).

The scanner 104-1 includes an enclosure 202 extending between a distal end portion 204 and a proximal end portion 206. The enclosure 202 includes a central axis 208 (e.g., longitudinal axis) that intersects the distal end portion 204 and the proximal end portion 206. The central axis 208 corresponds to an axial direction of the scanner 104-1. The scanner 104-1 is electrically coupled to an ultrasound imaging system (e.g., the ultrasound machine 102) via a coupling 210. In one example, the coupling 210 includes a cable that is attached to the proximal end portion 206 of the scanner 104-1 by a strain-relief element 212. In some implementations, the coupling 210 includes a wireless coupling so that the scanner 104-1 is wirelessly coupled to the ultrasound imaging system and communicates with the ultrasound imaging system via one or more wireless transmitters, receivers, or transceivers over a wireless connection or network (e.g., Bluetooth™, Wi-Fi™, etc.).

A transducer assembly 214 having two or more simultaneous transducer elements, or two or more simultaneous transducer arrays, is electrically coupled to system electronics 216 of the ultrasound machine 102. In operation, the transducer assembly 214 transmits ultrasound energy (e.g., ultrasound signals) from one or more of the simultaneous transducer elements toward a subject and receives ultrasound echoes (e.g., reflected ultrasound signals) from the subject. The ultrasound echoes are converted into electrical signals by the transducer element(s) and electrically transmitted to the system electronics 216 of the ultrasound machine 102 for processing and generation of one or more ultrasound images.

Capturing ultrasound data from a subject using a transducer assembly (e.g., the transducer assembly 214) generally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 Megahertz (MHz)) and/or high-frequency ultrasound (e.g., greater than or equal to 15 MHz). A particular frequency range to use can readily be determined based on various factors, including, for example, depth of imaging, desired resolution, and so forth. In some embodiments, a first transducer array of the transducer assembly 214 transmits first ultrasound signals focused at a first depth and a second transducer array of the transducer assembly 214 transmits second ultrasound signals focused at a second depth that differs from the first depth. As an example, the first ultrasound signals can be focused at a depth of approximately ten (10) centimeters or less into an anatomy of a subject and the second ultrasound signals can be focused at a depth of approximately thirty (30) centimeters or less into the anatomy of the subject. In an embodiment, the transducer assembly 214 can include a linear transducer array and a phased transducer array.

In some implementations, the system electronics 216 include one or more processors (e.g., the processor(s) 106 from FIG. 1), integrated circuits, application-specific integrated circuits (ASICs), field-programmable gate arrays (FPGAs), and power sources to support functioning of the ultrasound machine 102. In some implementations, the ultrasound machine 102 also includes an ultrasound-control subsystem 218 having one or more processors. At least one processor, FPGA, or ASIC can cause electrical signals to be transmitted to the transducer(s) of the scanner 104-1 to emit sound waves and receives electrical pulses from the scanner 104-1 that were created from the returning echoes. One or more processors, FPGAs, or ASICs can process the data associated with the received electrical pulses and form an image that is sent to an ultrasound imaging subsystem 220, which causes the image (e.g., the image 118 in FIG. 1) to be displayed via the display device 108. Thus, the display device 108 displays ultrasound images from the ultrasound data processed by the processor(s) of the ultrasound-control subsystem 218. The ultrasound images can include a first ultrasound image based on data associated with received reflected ultrasound signals from a first transducer array and a second ultrasound image based on data associated with received reflected ultrasound signals from a second transducer array.

In some implementations, the ultrasound machine 102 also includes one or more user input devices (e.g., a keyboard, a cursor control device, a microphone, a camera, a touchscreen, etc.) that input data and enable taking measurements from the display device 108 of the ultrasound machine 102. The ultrasound machine 102 can also include a disk storage device (e.g., computer-readable storage media such as read-only memory (ROM), a Flash memory, a dynamic random-access memory (DRAM), a novel object recognition (NOR) memory, a static random-access memory (SRAM), a NAND memory, and so on) for storing the acquired ultrasound data. In aspects, the disk storage device includes the memory 110, which is local to the ultrasound machine 102. Alternatively, the memory 110 used for storing the acquisition data can be remote, such as on a remote server communicatively connected to the ultrasound machine 102. In addition, the ultrasound machine 102 can include a printer that prints the ultrasound image from the displayed data. To avoid obscuring the techniques described herein, such user input devices, disk storage devices, and printer are not shown in FIG. 2.

The ultrasound scanner 104-1 in the illustrated example also includes one or more pressure sensors 222 on a lens of the scanner 104-1 and one or more pressure sensors 224 on the enclosure 202 of the scanner 104-1. The pressure sensors 222 and 224 can include in, on, or under a sensor region any suitable type of sensors for determining a pressure. In one example, the pressure sensors 222 and 224 include capacitive sensors that can measure a capacitance, or change in capacitance, caused by a user's touch or proximity of touch, as is common in touchscreen technologies. The pressure sensors 222 and 224 can generate sensor data indicative of a touch or pressure. The sensor data can include a binary indicator that indicates the presence and absence of a touch on the sensor. For instance, a "1" for sensor data can indicate that a pressure or touch is sensed at the pressure sensor, and a "0" for the sensor data can indicate that a pressure or touch is not sensed at the pressure sensor. Additionally, or alternatively, the sensor data can include a multi-level indicator that indicates an amount of pressure on the sensor, such as an integer scale from zero to five. For instance, a "0" can indicate that no pressure is detected at the sensor, and a "1" can indicate a small amount of pressure is detected at the sensor. A "2" can indicate a larger amount of pressure is detected at the sensor than a "1", and a "5" can indicate a maximum amount of pressure is detected at the sensor. A "3" and a "4" can indicate a pressure amount is detected with the pressure amount being between the maximum amount of pressure and the pressure corresponding to a "2".

The pressure sensors 222 and 224 are illustrated in FIG. 2 as ellipses for clarity and generally can be of any suitable shape and size and generate sensor data indicating pressure at any suitable number of points. For instance, in one example, the pressure sensors 222 cover an exterior surface of the lens of the scanner 104-1 and can be used to determine when the scanner 104-1 is placed against a patient. Additionally, or alternatively, the pressure sensors 224 can substantially cover the enclosure 202 of the scanner 104-1 and can be used to determine when a clinician grabs the scanner 104-1 for use in an ultrasound examination (e.g., the clinician has a suitable grip on the scanner 104-1 to perform the ultrasound examination). The ultrasound system 200 can use the sensor data from one or both of the pressure sensors 222 and 224 to generate a trigger signal that can be used for performing an ultrasound with simultaneous transducer arrays. For instance, when the sensor data from one or both of the pressure sensors 222 and 224 is above a threshold level, and/or the sensor data from the pressure sensors 224 indicates a grip pattern indicative of a human operating the scanner 104-1, the system 200 can generate a trigger signal. The trigger signal can be used to cause the ultrasound system 200 to enable one or more machine-learned models.

In embodiments, the scanner 104-1 includes an inertial measurement unit (IMU) 226 for generating positional data that determines a position and orientation of the scanner 104-1 in a coordinate system (e.g., the coordinate system 228) in FIG. 2. The IMU 226 can include a combination of accelerometers, gyroscopes, and magnetometers and generate positional data including data representing six degrees of freedom (6DOF), such as yaw, pitch, and roll angles in the coordinate system. Typically, 6DOF refers to the freedom of movement of a body in three-dimensional space. For example, the body is free to change position as forward/backward (surge), up/down (heave), and left/right (sway) translation in three perpendicular axes, combined with changes in orientation through rotation about three perpendicular axes, often termed yaw (normal axis), pitch (transverse axis), and roll (longitudinal axis). Additionally, or alternatively, the ultrasound system 200 can include a camera and fiducial markers on the scanner 104-1 (not shown in FIG. 2) to determine the positional data for the ultrasound scanner 104-1. In one example, the system 200 generates, based on the positional data, a trigger signal as described above. For instance, the positional data can indicate that the scanner 104-1 is within a threshold distance of the patient, and the trigger signal can be used by the ultrasound system 200 to enable one or more machine-learned models, such as a machine-learned model to identify and/or segment an anatomy in an ultrasound image.

A trigger signal generated by the system 200 (e.g., due to pressure data and/or positional data as described above) can cause a first transducer array of the scanner 104-1 to transmit first ultrasound signals, cause a second transducer array of the scanner 104-1 to transmit second ultrasound signals, or cause the first transducer array of the scanner 104-1 to transmit first ultrasound signals and the second transducer array of the scanner 104-1 to transmit second ultrasound signals. Additionally, or alternatively, the trigger signal can enable an examination preset that determines a respective operational mode for the first transducer array and the second transducer array of the scanner 104-1. In one embodiment, the trigger signal enables a first protocol for the first transducer array and a second protocol for the second transducer array. In an embodiment, the trigger signal can enable a machined-learned model to identify a target for an interventional instrument (e.g., the interventional instrument 606 depicted in FIG. 6) detected within data of reflected ultrasound signals of the first ultrasound signals. In yet another embodiment, the trigger signal can enable a threshold depth and cause the ultrasound system to automatically transition from the first transducer array to the second transducer array when an interventional instrument, detected within the first ultrasound data, reaches the predetermined depth. Additionally, or alternatively, the trigger signal can cause the ultrasound system to automatically replace a first ultrasound image, based on data corresponding to the first ultrasound signals, with a second ultrasound image, based on data corresponding to the second ultrasound signals.

Figure 3:
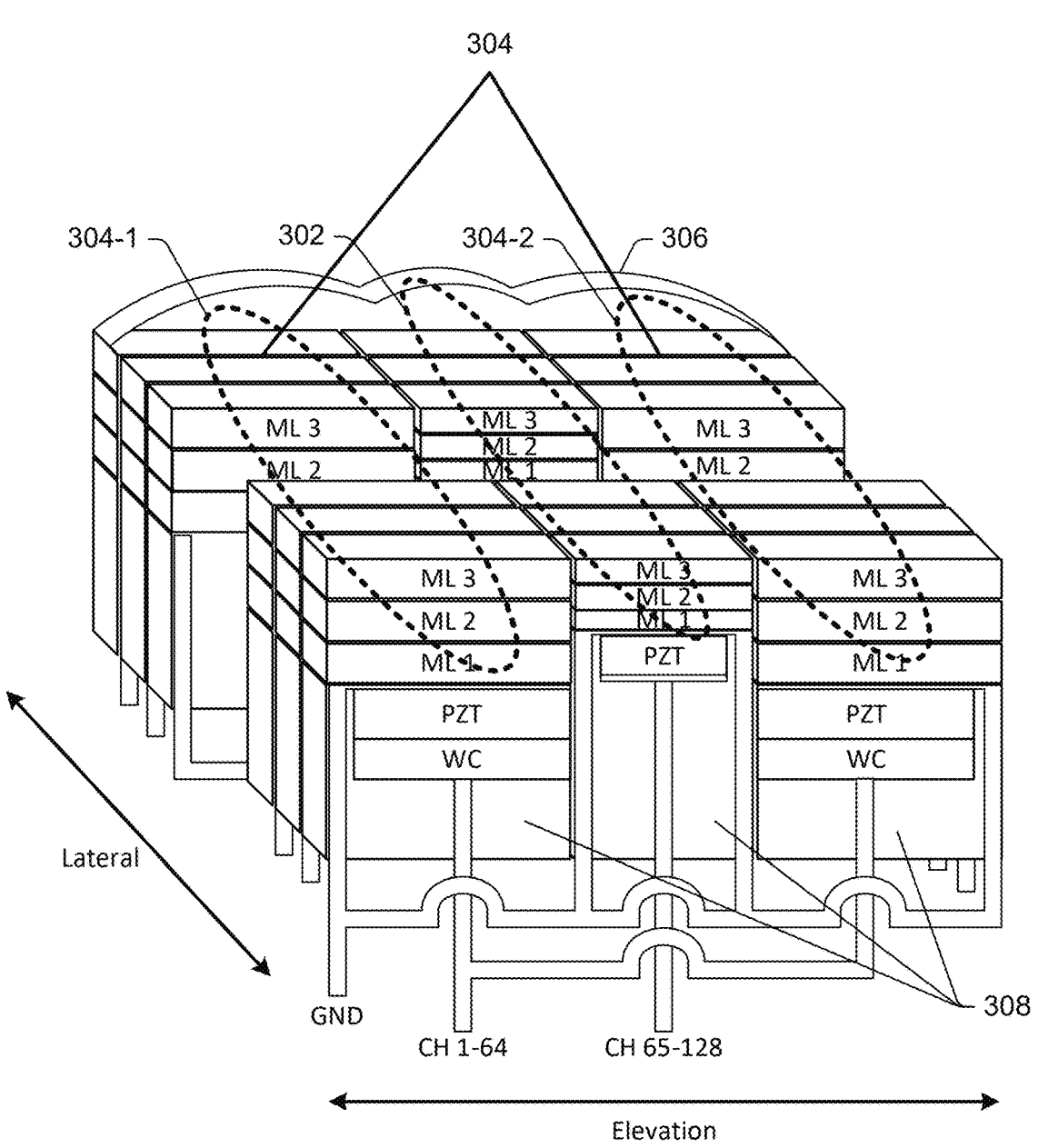
FIG. 3 illustrates an example multi-array transducer for an ultrasound device or system with simultaneous transducer arrays.

FIG. 3 illustrates an example multi-array transducer 300 for an ultrasound device, or ultrasound system, having simultaneous transducer arrays. For example, the multi-array transducer 300 can be included in a multi-array scanner (e.g., the scanner 104) and can include at least two arrays, such as a first transducer array 302 and a second transducer array 304. The second transducer array 304 can include a first transducer sub-array 304-1 and a second transducer sub-array 304-2. The first transducer array 302 can be referred to as a center transducer array, as it is located between the first transducer sub-array 304-1 and the second transducer sub-array 304-2 of the second transducer array 304. In the example multi-array transducer 300, the transducer arrays 302, 304 are laid out in rows, parallel to one another. However, multi-array transducers in accordance with the disclosed implementations are not so limited and can be arranged in any suitable configuration. For example, transducer array configurations can include a circular transducer array configuration (e.g., transducer arrays arranged in concentric circles or ellipses), a polygonal transducer array configuration (e.g., transducer arrays arranged in concentric polygons, such as nested triangles), an open-shaped transducer array configuration (e.g., nested "L" or "V" shaped transducer arrays), and a matrix transducer array configuration (e.g., a configuration that includes a center transducer array with elements on a grid, and a surrounding transducer array that includes transducer array elements that are also on the grid and that surround the center transducer array).

The example multi-array transducer 300 can also include an acoustic lens (e.g., lens 306) that covers the two transducer arrays 302, 304. In the example in FIG. 3, the lens 306 includes multiple radii of curvature. For example, a first radius covers the first transducer array 302, a second radius covers the first transducer sub-array 304-1 of the second transducer array 304, and a third radius covers the second transducer sub-array 304-2 of the second transducer array 304. In an example, the second radius and the third radius are the same radius, which is different from the first radius. In other embodiments, the lens 306 can include a single radius of curvature that covers the two transducer arrays 302, 304.

In the example in FIG. 3, the transducer arrays 302, 304 of the multi-array transducer 300 include array elements of PZT ceramic material with piezoelectric properties and acoustic matching layers (ML 1, ML 2, ML 3, etc.). However, multi-array transducers in accordance with the present disclosure are not so limited and can include transducer arrays in any suitable combination of PZT, PMUT, and CMUT transducer array elements. In one example, the center transducer array (e.g., the first transducer array 302) can include PZT transducer array elements, and an adjacent transducer array (e.g., the first transducer sub-array 304-1 and the second transducer sub-array 304-2 of the second transducer array 304) can include PMUT transducer array elements. In another example, the center transducer array can include PZT transducer array elements, and the adjacent transducer array can include CMUT transducer array elements. In another example, the center transducer array can include PMUT transducer array elements, and the adjacent transducer array can include CMUT transducer array elements. In another example, the center transducer array can include PMUT transducer array elements, and the adjacent transducer array can include PZT transducer array elements. In another example, the center transducer array can include CMUT transducer array elements, and the adjacent transducer array can include PMUT transducer array elements. In another example, the center transducer array can include CMUT transducer array elements, and the adjacent transducer array can include PZT transducer array elements. In aspects, the transducer array elements are stacked between a backing material 308 and the lens 306.

In embodiments, the first transducer array 302 operates at a first frequency, and the second transducer array 304 operates at a second frequency that differs from the first frequency. For instance, the second frequency can be lower than the first frequency. Alternatively, the second frequency can be higher than the first frequency. In some embodiments, the first transducer array 302 and the second transducer array 304 can be different types of transducer arrays. For example, the first transducer array 302 can be a linear transducer array and the second array 304 can be a phased transducer array. In some embodiments, the first transducer array 302 can be configured to transmit first ultrasound signals focused at a first depth and the second transducer array 304 can be configured to transmit second ultrasound signals focused at a second depth differing from the first depth. In an embodiment, the first depth can be approximately ten (10) centimeters or less into an anatomy of a subject and the second depth can be approximately thirty (30) centimeters or less into the anatomy of the subject.

Figure 4:
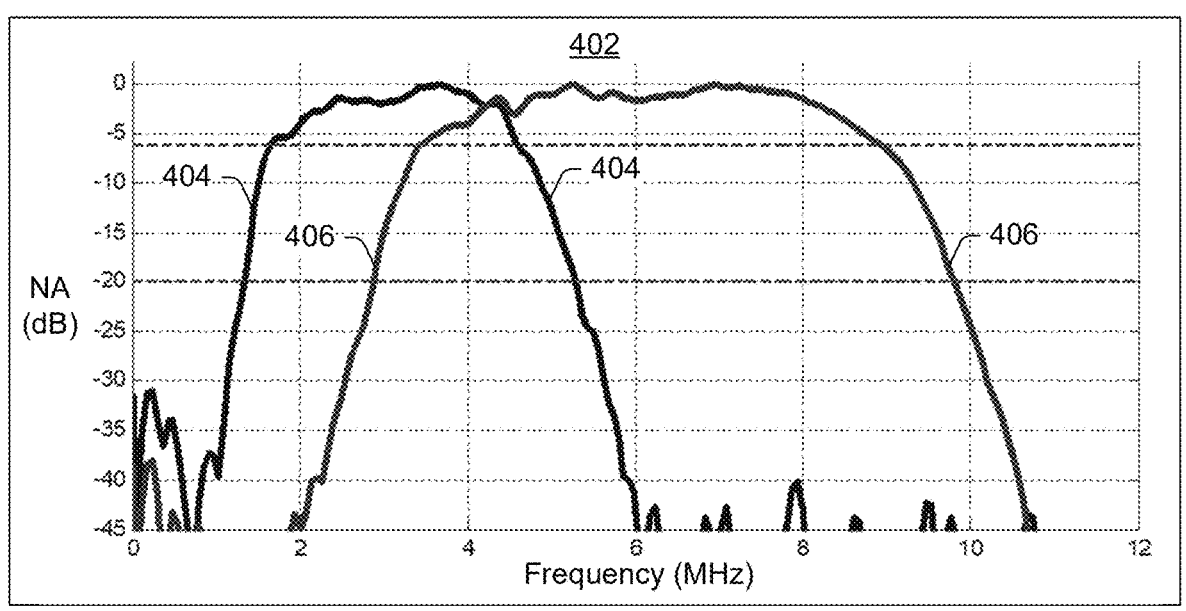
FIG. 4 illustrates example characteristics of a multi-array transducer for an ultrasound system with simultaneous transducer arrays.
Figure 4:
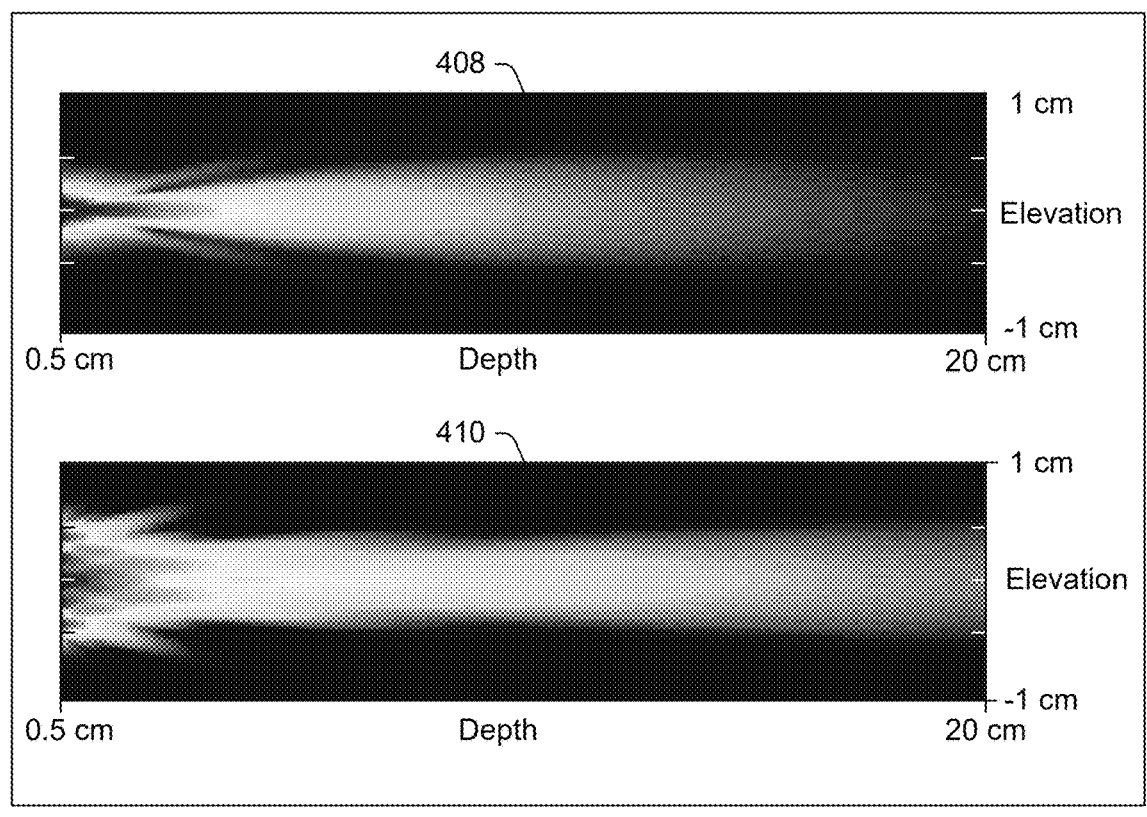

For example, FIG. 4 illustrates example characteristics 400 of a multi-array transducer usable for ultrasound devices with simultaneous arrays. The graph illustrated in FIG. 4 illustrates the characteristics regarding frequency measured in megahertz (MHz) (shown on the x-axis) and the normalized amplitude measured in decibels (dB) (shown on the y-axis). The characteristics 400 include a frequency response 402 of a multi-array transducer, such as the multi-array transducer 300 in FIG. 3. The frequency response 402 includes a first bandwidth 404 and a second bandwidth 406. The first bandwidth 404 illustrates a frequency response of a transducer array, such as the second transducer array 304 in FIG. 3, and the second bandwidth 406 illustrates a frequency response of another transducer array, such as the first transducer array 302 in FIG. 3.

The characteristics 400 also include illustrations of a first ultrasound beam 408 and a second ultrasound beam 410 showing depth against elevation. The first ultrasound beam 408 corresponds to the first transducer array 302 in FIG. 3 and the second ultrasound beam 410 corresponds to the second transducer array 304 in FIG. 3. In this example, because the first transducer array 302 is implemented to operate at a higher frequency than the second transducer array 304, the second ultrasound beam 410 has deeper penetration than the first ultrasound beam 408, but the first ultrasound beam 408 has better focus than the second ultrasound beam 410. Hence, the multi-array transducer can exploit the different ultrasound beam profiles associated with the multiple arrays to image at multiple depths with the same ultrasound scanner, rather than requiring the use of multiple ultrasound scanners. Thus, personnel can perform a full-body ultrasound scan of a patient with a single scanner, without the need to utilize multiple scanners, thus saving time and resources, reducing the chances of infection due to scanner change, and providing a superficial image and a deep image in substantially the same imaging plane. In an embodiment, the first transducer array 302 or the second transducer array 304 of FIG. 3 are configured to be selectively rotated (e.g., by ninety (90) degrees) so that the superficial image and the deep image are no longer within the same imaging plane.

Moreover, because the transducer can include multiple arrays of different types of array elements (e.g., PZT, PMUT, and CMUT), the strengths of each of the types of array elements can be exploited. For example, PMUT, which conventionally has better transmit sensitivity than CMUT, can be used for ultrasound transmission, while CMUT, which conventionally has better receive sensitivity than PMUT, can be used for ultrasound reception.

Figure 5:
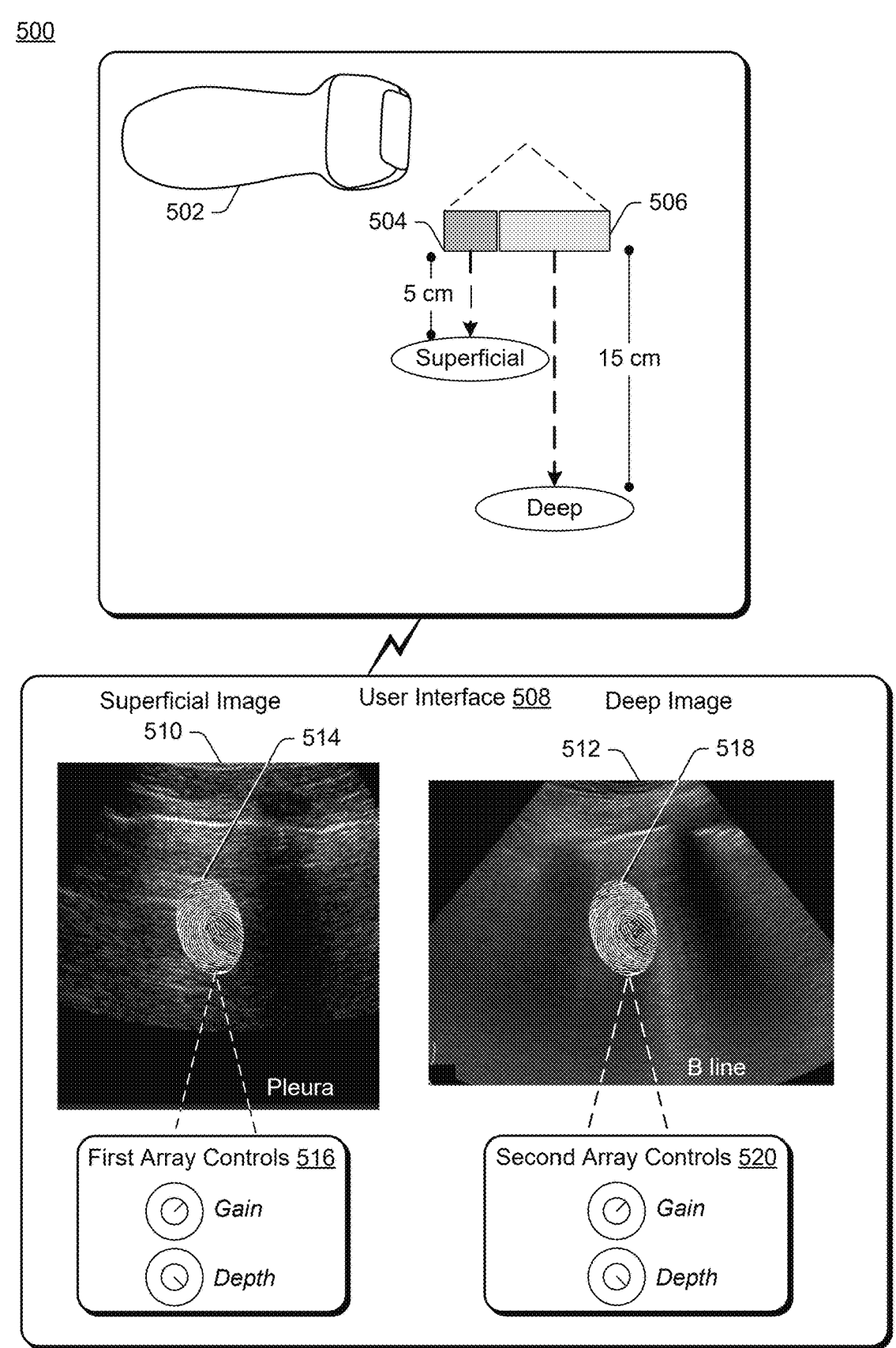
FIG. 5 illustrates an example system for an ultrasound device with simultaneous transducer arrays.

FIG. 5 illustrates an example ultrasound system 500 for ultrasound examinations with simultaneous transducer arrays. The system 500 includes an ultrasound scanner 502. The ultrasound scanner 502 is an example of the ultrasound scanner 104 that includes simultaneous transducer arrays. The ultrasound scanner 502 is a multi-array scanner and includes a first transducer array 504 and a second transducer array 506. In an embodiment, the first transducer array 504 includes a linear transducer array and can be configured for imaging superficial depths (e.g., from 0 to 5 cm), and the second transducer array 506 includes a phased transducer array and can be configured to image greater depths (e.g., from 0 to 15 cm). The first transducer array 504 and the second transducer array 506 are examples of the transducer arrays 302, 304 in FIG. 3.

The ultrasound scanner 502 is coupled to a user interface 508. The user interface 508 can be implemented on any suitable computing device, including the ultrasound machine 102, and, in some embodiments, the ultrasound system 500. In embodiments, the user interface 508 is implemented on the display device 108. The user interface 508 can also be implemented on a touchscreen.

The user interface 508 is configured to display a first ultrasound image 510 and a second ultrasound image 512. The user interface 508 can be configured to display the first ultrasound image 510 and the second ultrasound image 512 simultaneously in real time. The first ultrasound image 510 can correspond to first data received from the ultrasound scanner 502 from reflected ultrasound signals of ultrasound signals transmitted from the first transducer array 504 and the second ultrasound image 512 can correspond to second data received from the ultrasound scanner 502 from reflected ultrasound signals of ultrasound signals transmitted from the second transducer array 506. In embodiments, the ultrasound scanner 502 enables the first transducer array 504 and the second transducer array 506 for simultaneous operation, and the user interface 508 can simultaneously display the first ultrasound image 510 and the second ultrasound image 512.

In the example illustrated in FIG. 5, a user selects the first image 510, such as via a touch input 514. Responsive to the touch input 514, the user interface 508 displays a first array controls panel 516. The first array controls panel 516 can display any suitable control, option, or selection for controlling and/or configuring the first transducer array 504. For example, the first array controls panel 516 can display gain and depth controls for configuring the first transducer array 504. For example, a user input to the gain control or the depth control can adjust the gain or the depth, respectively, that is used by the first transducer array 504 of the ultrasound scanner 502 to generate the ultrasound data used by the system 500 to generate the first image 510. Further, a user selects the second image 512, such as via a touch input 518. Responsive to the touch input 518, the user interface 508 displays a second array controls panel 520. The second array controls panel 520 can display any suitable control, option, or selection for controlling and/or configuring the second transducer array 506. For example, the second array controls panel 520 can display gain and depth controls for configuring the second transducer array 506. In an example, a user input to the gain control or depth control can adjust the gain or the depth, respectively, that is used by the second transducer array 506 of the ultrasound scanner 502 to generate the ultrasound data used by the system 500 to generate the second image 512.

Figure 6:
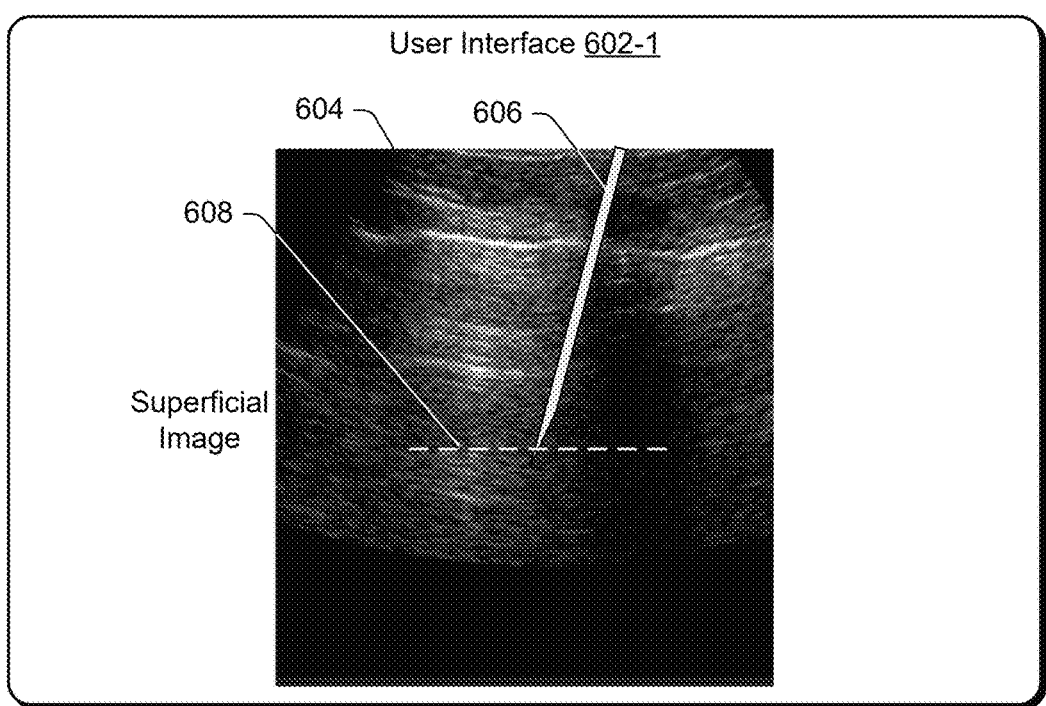
FIG. 6 illustrates example user interfaces for an ultrasound system with simultaneous transducer arrays.
Figure 6:
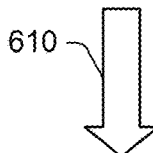
Figure 6:
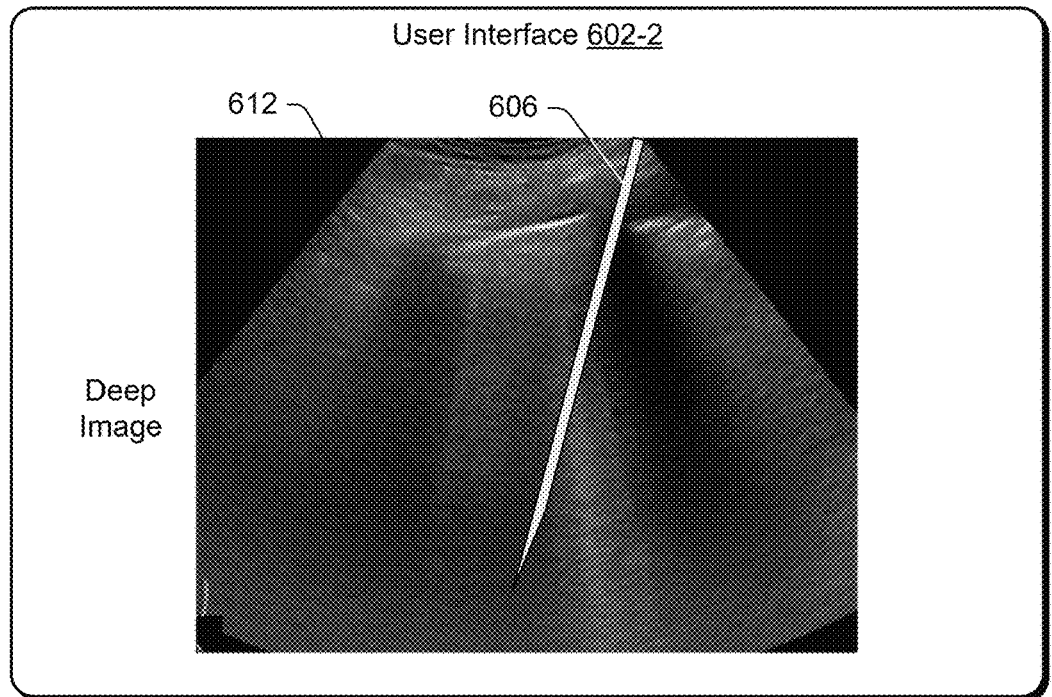

FIG. 6 illustrates example user interfaces 600 for an ultrasound system (e.g., ultrasound system 100, ultrasound system 200, ultrasound system 500), or ultrasound device (e.g., ultrasound machine 102), having simultaneous transducer arrays. The user interfaces 600 include a first user interface 602-1 and a second user interface 602-2. The first user interface 602-1 includes a first ultrasound image 604, which is an example of a superficial ultrasound image (e.g., corresponding to superficial depths of 0-10 cm) that is captured using a first transducer array 504 (e.g., a linear transducer array). The first ultrasound image 604 depicts an interventional instrument 606 (e.g., a needle, scope, injector, extractor, forceps, cutter, catheter, etc.) that has been or is being inserted into a patient. When a tip of the interventional instrument 606 reaches a threshold depth 608, the first user interface 602-1 is updated to the second user interface 602-2, as is indicated by an arrow 610. In other words, the ultrasound system, or ultrasound device, can be configured to automatically replace the first user interface 602-1 with the second user interface 602-2 upon the interventional instrument 606 reaching the threshold depth 608. Upon replacement, the first image 604 ceases to be displayed in the first user interface 602-1.

The threshold depth 608 can be set by a user or can be determined by the ultrasound system. For example, the ultrasound system can determine a region of interest (ROI) or anatomy that the user is targeting with the interventional instrument 606 and automatically and without user intervention set the threshold depth 608 based on the ROI or anatomy. The ultrasound system can determine the threshold depth 608 so that the user interface 602-1 is updated to the user interface 602-2 when the tip of the interventional instrument 606 reaches the threshold depth 608, the ROI, and/or the anatomy or just before the tip of the interventional instrument 606 reaches the threshold depth 608, ROI, and/or anatomy.

In some aspects, in the second user interface 602-2, the first ultrasound image 604 from the first user interface 602-1 is replaced with the second ultrasound image 612. The second ultrasound image 612 also depicts the interventional instrument 606, but at a greater depth than depicted in the first ultrasound image 604. The second ultrasound image 612 is an example of a deep ultrasound image (e.g., corresponding to depths of 0-30 cm) that is captured using a second transducer array 506 (e.g., a phased transducer array).

In embodiments, the ultrasound system automatically enables the second transducer array 506 based on the position of the tip of the interventional instrument 606 relative to the threshold depth 608. For instance, as the tip of the interventional instrument 606 is approaching the threshold depth 608, the ultrasound system can activate the second transducer array 506 to ensure a smooth transition from displaying the first ultrasound image 604 to displaying the second ultrasound image 612. In embodiments, the first ultrasound image 604 and the second ultrasound image 612 depict the same imaging plane or similar imaging planes. Hence, the interventional instrument 606 can be in-plane in both the first ultrasound image 604 and the second ultrasound image 612. A multi-array ultrasound scanner (such as the ultrasound scanner 502 of FIG. 5) that utilizes simultaneous transducer arrays 504, 506 can enable the first ultrasound image 604 and the second ultrasound image 612 to be co-registered in substantially the same plane, as a single multi-array ultrasound scanner can be used during a single ultrasound examination while providing the first ultrasound image 604 based on data from a first transducer array of the multi-array ultrasound scanner and the second ultrasound image 612 based on data from a second transducer array of the multi-array ultrasound scanner.

In embodiments, the ultrasound system can automatically activate the second transducer array based on the depth into the subject's anatomy of the tip of the interventional instrument 606. A processor system (e.g., that implements a machine-learned model) can determine when to automatically activate the second transducer array based on the depth into the subject's anatomy of the tip of the interventional instrument 606. In another embodiment, the ultrasound system can automatically replace the first ultrasound image 604 with the second ultrasound image 612 based on the depth into the subject's anatomy of the tip of the interventional instrument 606. For example, the first transducer array and the second transducer array can both be activated simultaneously with the ultrasound system only displaying the first ultrasound image 604 until automatically switching to display the second ultrasound image 612. Alternatively, the ultrasound system can automatically display the second ultrasound image 612 simultaneously with the first ultrasound image 604 based on the depth into the subject's anatomy of the tip of the interventional instrument 606.

Figure 7:
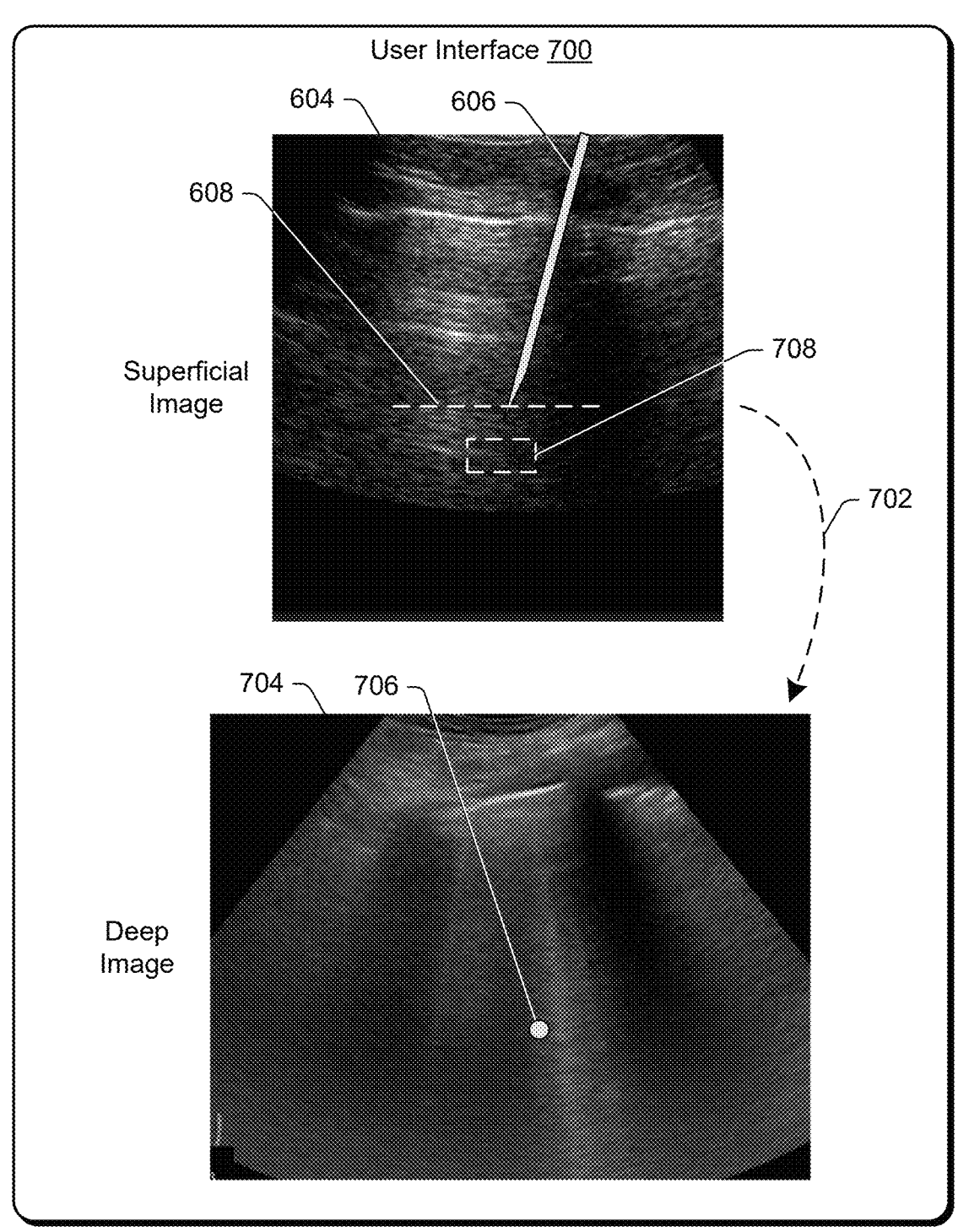
FIG. 7 illustrates an example user interface for an ultrasound system with simultaneous transducer arrays.

FIG. 7 illustrates an example user interface 700 for ultrasound with simultaneous transducer arrays. The user interface 700 includes the first ultrasound image 604 from FIG. 6. In this example, however, as the tip of the interventional instrument 606 approaches the threshold depth 608 (or, in some embodiments, crosses the threshold depth 608), the user interface enables (as evidenced by an arrow 702) the display of a second ultrasound image 704.

The second ultrasound image 704 can be generated from ultrasound data captured by a different transducer array than the transducer array used to generate the first ultrasound image 604, such as a phased transducer array (e.g., the second transducer array 506 of FIG. 5). The second ultrasound image 704 is an example of a deep ultrasound image (e.g., corresponding to depths of 0-30 cm). The second ultrasound image 704 also depicts a tip 706 of the interventional instrument 606, but in this example, the imaging plane of the second ultrasound image 704 is not the same as the imaging plane of the first ultrasound image 604, and hence the interventional instrument 606 in the second ultrasound image 704 is out-of-plane with respect to the first ultrasound image 604. In embodiments, the user interface 700 simultaneously displays the first ultrasound image 604 and the second ultrasound image 704.

In the user interface 700, an area 708 is depicted in the first ultrasound image 604. The area 708 can include an ROI or anatomy of a subject that can be user selected or determined by the ultrasound system (e.g., with one or more machine-learned models). Based on the depth within the anatomy of the subject that the area 708 is located, the ultrasound system can set a focus depth of one or more transducer arrays (e.g., first transducer array 504 and second transducer array 506) used to generate one or more of the first ultrasound image 604 of FIGS. 6 and 7, the second ultrasound image 612 of FIG. 6, or the second ultrasound image 704 of FIG. 7. The system can enable a user to select the threshold depth 608 and/or the area 708. Alternatively, a machined-learned model can automatically determine the area 708 based on a selected threshold depth 608 or can determine the area 708 based on the anatomy of the subject.

FIG. 8-1 illustrates an example system 800-1 for ultrasound with simultaneous transducer arrays. The system 800-1 includes a superficial ultrasound image 802, which is an example of the ultrasound image 510 that can be captured based on data from a linear transducer array, and a deep ultrasound image 804, which is an example of the ultrasound image 512 that can be captured based on data from a phased transducer array. The superficial ultrasound image 802 and the deep ultrasound image 804 are provided as input to a machine-learned model 806 (or more generally, a processor system that can implement the machine-learned model 806 or any suitable algorithm for fusing images), which processes the superficial ultrasound image 802 and the deep ultrasound image 804 to generate a fused ultrasound image 808. The fused ultrasound image 808 can include any suitable representation of the image content of the superficial ultrasound image 802 and the image content of the deep ultrasound image 804. For example, a fused ultrasound image 808-1 and a fused ultrasound image 808-2 are examples of the fused ultrasound image 808.

The fused ultrasound image 808-1 includes content interior to a boundary 810 and content exterior to the boundary 810. The content that is interior to the boundary 810 can be based on the deep ultrasound image 804, and the content that is exterior to the boundary 810 is taken from the superficial ultrasound image 802. In the fused ultrasound image 808-2, the content from the deep ultrasound image 804 is appended below the content from the superficial ultrasound image 802. The fused ultrasound images 808-1 and 808-2 are meant to be exemplary and non-limiting. Generally, the fused ultrasound image 808 can include any suitable representation for the content of the superficial ultrasound image 802 and the deep ultrasound image 804, including the blending of pixel content, content segmentation, picture-in-picture, superposition of image content with a common field of view, etc.

FIG. 8-2 illustrates an example system 800-2 for ultrasound with simultaneous transducer arrays. The system 800-2 includes a superficial ultrasound image 802, which is an example of the ultrasound image 510 that can be captured based on data from a linear transducer array, and a deep ultrasound image 804, which is an example of the ultrasound image 512 that can be captured based on data from a phased transducer array. The superficial ultrasound image 802 and the deep ultrasound image 804 are provided as input to a machine-learned model 806, which processes the superficial ultrasound image 802 and the deep ultrasound image 804 to generate a fused ultrasound image 808. The fused ultrasound image 808 can include any suitable representation of the image content of the superficial ultrasound image 802 and the image content of the deep ultrasound image 804. For example, a fused ultrasound image 808-3 is yet another example of the fused ultrasound image 808.

In the fused ultrasound image 808-3, a portion of the content from the deep ultrasound image 804 is overlaid with a portion of the content from the superficial ultrasound image 802. The fused ultrasound image 808-3 can provide increased definition (e.g., better resolution) at shorter depths to a deep ultrasound image. Alternatively, the fused ultrasound image 808-3 can provide greater depth to a superficial ultrasound image. However, the greater depth to the superficial ultrasound image will result in a decreased definition (e.g., lower resolution). These results can be accomplished by overlaying a portion of an ultrasound image having better definition (e.g., superficial image 802) with a portion of an ultrasound image penetrating deeper into the anatomy (e.g., deep ultrasound image 804) that provides less definition. The fused ultrasound image 808-3 is meant to be exemplary and non-limiting.

FIG. 8-3 illustrates an example system 800-3 for ultrasound with simultaneous transducer arrays. Various ultrasound transducers can be used for ultrasound with simultaneous transducer arrays as would be appreciated by one of ordinary skill in the art having the benefit of this disclosure. For example, one ultrasound transducer array of the simultaneous transducer arrays can be a color-transducer array configured to generate data from which a color image 802-1 can be generated and another ultrasound transducer array of the simultaneous transducer arrays can be configured to generate data from which a deep image 804 can be generated. For example, one of the transducer arrays of the simultaneous transducer arrays can be a doppler transducer array or an ultrahigh-frequency transducer array. The system 800-3 includes a color ultrasound image 802-1, which can be captured based on data from an ultrasound transducer array configured to capture data to generate such an image. A color ultrasound image can be used to visually represent fluid (e.g., blood motion, blood flow) within an anatomy in an ultrasound image. For example, the color image 802-1 can include a first color flow 812 and a second color flow 814. The first color flow 812 and the second color flow 814 can, in some examples, represent fluid, such as a blood, flowing in opposite directions. The color image 802-2 is shown as a rectangle for illustrative purposes but can be formed in other shapes, such as a trapezoid.

The system 800-3 also includes the deep ultrasound image 804, which can be captured based on data from a phased transducer array. The color ultrasound image 802-1 and the deep ultrasound image 804 are provided as input to a machine-learned model 806, which processes the color ultrasound image 802-1 and the deep ultrasound image 804 to generate a fused ultrasound image 808. The fused ultrasound image 808 can include any suitable representation of the image content of the color ultrasound image 802-1 and the image content of the deep ultrasound image 804. For example, a fused ultrasound image 808-4 is yet another example of the fused ultrasound image 808.

The overlaying of a portion of a first image (e.g., color ultrasound image 802-1) with a portion of a second image (e.g., deep image 804) can enable ultrasound steering (e.g., spatial compounding) over for the overlapped portion of the images. The fused image 808-4 can enable ultrasound steering, on an ultrasound image that typically cannot be steered, for the overlapped portion of the ultrasound images. Ultrasound steering (e.g., spatial compounding) is an imaging technique in which multiple ultrasound images of a target are obtained from multiple vantage points (e.g., multiple angles) that are combined to form a single compounded ultrasound image. In order to produce such a single compounded ultrasound image, the ultrasound beams are steered using a set of predetermined angles.

Figure 9:
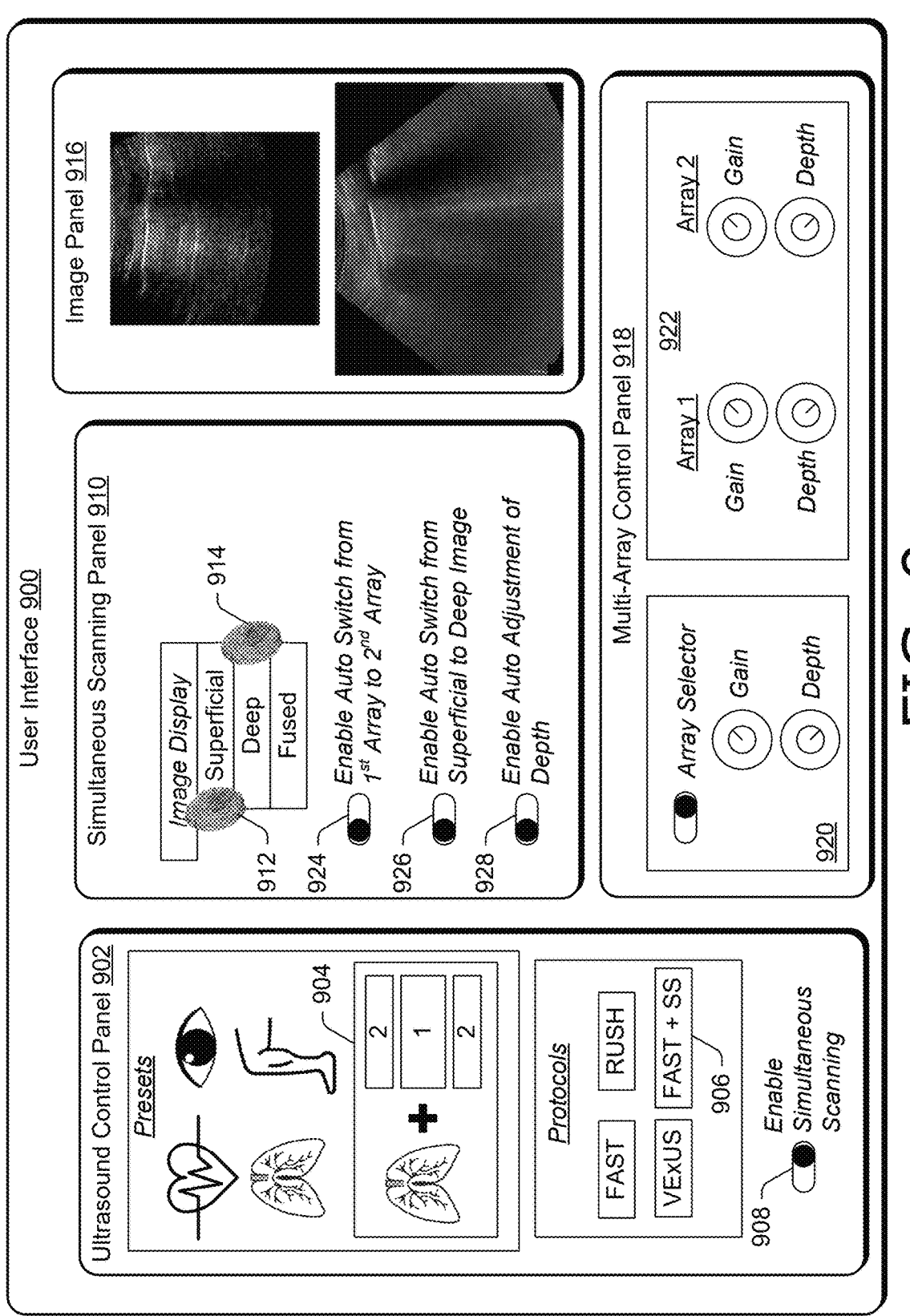
FIG. 9 illustrates an example user interface for an ultrasound system with simultaneous transducer arrays.

FIG. 9 illustrates an example user interface 900 for an ultrasound system having simultaneous transducer arrays. The user interface 900 includes an ultrasound-control panel 902, which can include any suitable controls for configuring an ultrasound system with simultaneous transducer arrays. In the example in FIG. 9, the ultrasound-control panel 902 includes ultrasound controls for selecting examination presets. The examination presets are represented by selectable icons. For example, the selectable icons can be for a cardiac examination, a respiratory examination, an ocular examination, and a muscular-skeletal examination. These examination presets, when selected, can configure the simultaneous transducer arrays with predetermined values of gain and depth and other imaging parameters (e.g., beamformer settings, filter coefficients, amplitude settings, etc.). The ultrasound-control panel 902 also includes an examination preset 904 for a respiratory examination with a multi-array scanner with simultaneous transducer arrays. For instance, the examination preset 904 can enable two or more transducer arrays of the multi-array scanner for simultaneous scanning, such as a first transducer array for superficial scanning (e.g., 0-10 cm) and a second transducer array for deep scanning (e.g., 0-30 cm). Hence, the user interface 900 can simultaneously display a superficial image and a deep image.

The ultrasound-control panel 902 also includes controls for selecting ultrasound protocols, including a Focused Assessment with Sonography for Trauma (FAST) protocol, a Rapid Ultrasound for Shock and Hypotension (RUSH) protocol, and a Venous Congestion Evaluation using Ultrasound (VExUS) protocol. A user can select one of these example protocols, and, in response, the system can configure itself for an examination in accordance with the protocol, including to display a protocol panel in the user interface 900 (not shown for clarity) with guided steps needed to complete the selected protocol. The ultrasound-control panel 902 also includes a protocol 906 for a FAST examination with simultaneous scanning, designated as FAST+SS. The protocol 906 (e.g., FAST+SS) can include guided steps for a multi-array scanner that includes a first transducer array for superficial scanning (e.g., 0-10 cm) and a second transducer array for deep scanning (e.g., 0-30 cm).

The ultrasound-control panel 902 also includes a selection 908 (e.g., an electronic rocker switch) to enable simultaneous ultrasound scanning in accordance with the present disclosure. For instance, responsive to the selection 908 being enabled, the user interface 900 can display a simultaneous-scanning panel 910. The simultaneous-scanning panel 910 can include any suitable control or setting for configuring the system for simultaneous scanning with a multi-array transducer scanner. In the example in FIG. 9, the simultaneous-scanning panel 910 includes a drop-down menu with selections for image display (e.g., what images generated by the multi-array scanner are enabled for simultaneous scanning) that the user would like to display. The drop-down menu includes selections to display a superficial image (e.g., the image 510), a deep image (e.g., the image 512), and a fused image (e.g., fused image 808-1, fused image 808-2, fused image 808-3, fused image 808-4). A user has selected both the superficial image and the deep image for display, as indicated by touch inputs 912 and 914, respectively. Accordingly, an image panel 916 simultaneously displays the superficial image and the deep image.

The simultaneous-scanning panel 910 also includes selections to configure the system in various automatic modes. For instance, the simultaneous-scanning panel 910 includes a selector 924 to enable an automatic switch from a first transducer array to a second transducer array. The first transducer array can be a linear array used for superficial imaging, and the second transducer array can be a phased array used for deep imaging. The switch from the first transducer array to the second transducer array can be based on a threshold depth of an interventional instrument (e.g., a needle). When a tip of the interventional instrument reaches the threshold depth, the ultrasound system can switch from the first transducer array to the second transducer array, including disabling the first transducer array and enabling the second transducer array. In other aspects, the selector 924 can enable the automatic switching from a first ultrasound image generated from reflection data (e.g., data from reflected ultrasound signals) from the first transducer array to a second ultrasound image generated from reflection data (e.g., data from reflected ultrasound signals) from the second ultrasound array. The threshold depth can be set by a user or determined by the ultrasound system (e.g., based on an anatomy or ROI in an ultrasound image). This selection can reduce heat and save battery life, compared to leaving both transducer arrays enabled at all times of scanning.

The simultaneous-scanning panel 910 includes a selector 926 to enable automatic switching from a superficial image to a deep image. The superficial image can be captured by a linear transducer array, and the deep image can be captured by a phased transducer array. When enabled, this selector 926 can change what image is displayed by the user interface, or how the images are displayed. For instance, a superficial ultrasound image can be replaced by a deep ultrasound image (as is illustrated in FIG. 6). In another example, a superficial ultrasound image is de-emphasized (e.g., reduced in size or highlighting removed) and a deep ultrasound image is emphasized (e.g., increased in size or highlighted), while both the superficial and the deep ultrasound image remain displayed by the user interface.

The simultaneous-scanning panel 910 includes a selector 928 to enable automatic adjustment of a focus depth of one or more transducer arrays. For example, the ultrasound system can determine an ROI in an ultrasound image or an anatomy in an ultrasound image. The ROI or anatomy can be user selected. Alternatively, the ultrasound system can automatically determine the ROI or anatomy, such as with a first machine-learned model to generate a classification label for an anatomy and a second machine-learned model to segment the anatomy. In one example, a user selects an ROI (e.g., draws a box on an ultrasound image), and the ultrasound system automatically determines an anatomy based on the ROI (e.g., that is included in the ROI). Based on the ROI or anatomy, the ultrasound system can set a gain and/or depth for one or more of the transducer arrays, including a first transducer array configured to generate reflection data from which a superficial ultrasound image can be generated and/or a second transducer array configured to generate refection data from which a deep ultrasound image can be generated. The automatic configuration of the transducer array(s) in this manner can assist a clinician when inserting an interventional instrument into the anatomy or ROI, by allowing the clinician to focus on the interventional instrument insertion without manually setting transducer array parameters.

The user interface 900 also includes a multi-array control panel 918, which can include any suitable control for manual adjustment of a transducer array. For instance, the multi-array control panel 918 includes a control option 920 that includes a single gain knob and a single depth knob that can be switched to control different transducer arrays. In contrast, a control option 922 includes a set of gain and depth knobs dedicated to one transducer array and another set of gain and depth knobs dedicated to another transducer array.

Figure 10:
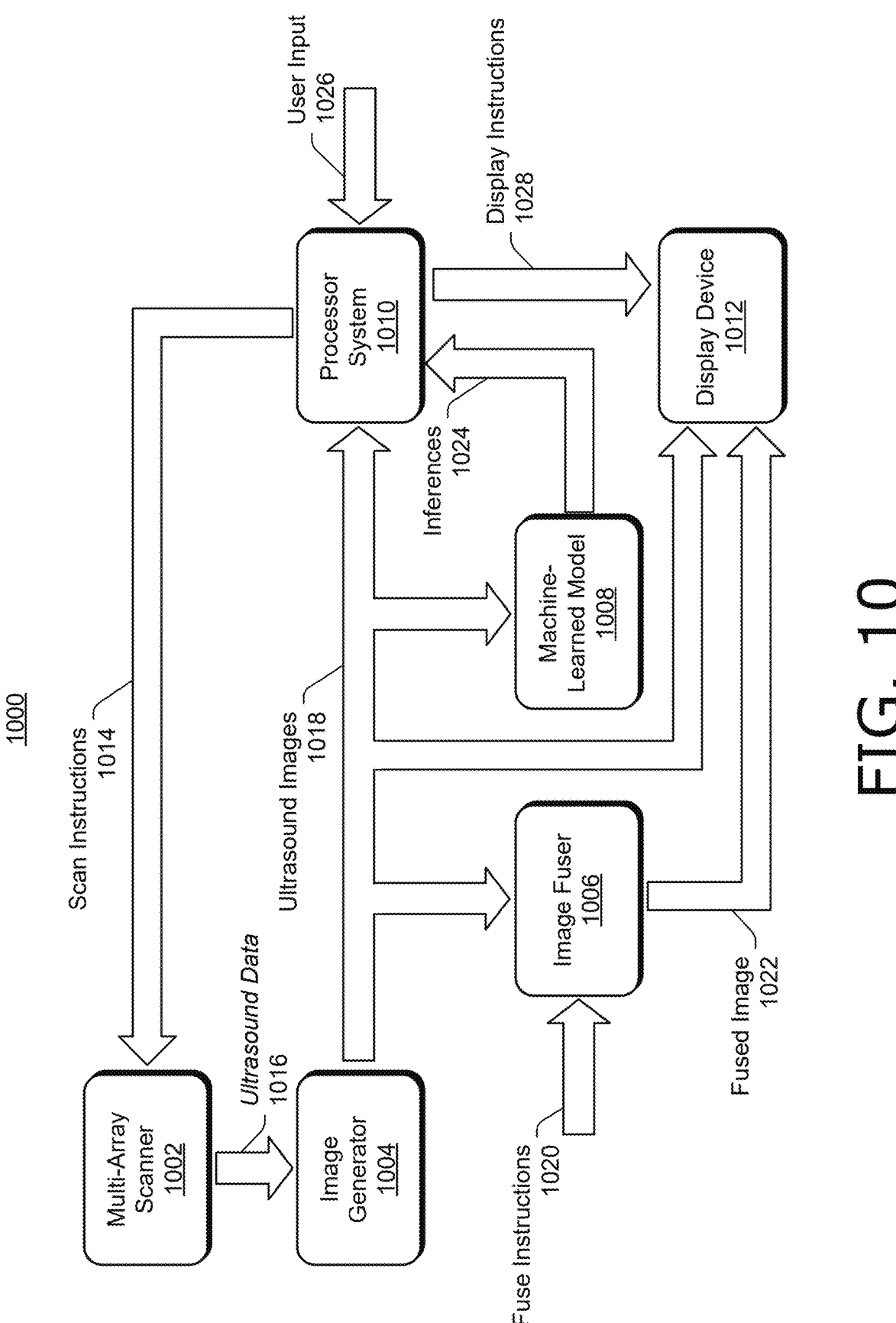
FIG. 10 illustrates an example ultrasound system with simultaneous transducer arrays.

FIG. 10 illustrates an example ultrasound system 1000 having simultaneous transducer arrays. The ultrasound system 1000 includes a multi-array scanner 1002 that includes simultaneous transducer arrays, an image generator 1004, an image fuser 1006, a machine-learned model 1008, a processor system 1010 (e.g., one or more processors), and a display device 1012.

The multi-array scanner 1002 is an example of the scanner 104 and the scanner 502 and can include a multi-array transducer assembly (e.g., the multi-array transducer 300). The multi-array scanner 1002 receives scan instructions 1014 from the processor system 1010 and generates ultrasound data 1016 according to the scan instructions 1014. The scan instructions 1014 can instruct the multi-array scanner with the simultaneous transducer arrays when to scan and when not to scan and include any suitable waveforms, parameters, and settings to generate the ultrasound data. The ultrasound data 1016 can include image data for a superficial ultrasound image generated using a first transducer array (e.g., a linear transducer array) of the multi-array scanner 1002 and image data for a deep ultrasound image generated using a second transducer array (e.g., a phased transducer array) of the multi-array scanner 1002. The multi-array scanner 1002 provides the ultrasound data to the image generator 1004.

The image generator 1004 generates ultrasound images 1018, including the superficial ultrasound image and the deep ultrasound image, from the ultrasound data. In an embodiment, the image generator 1004 in conjunction with the processor system 1010 can generate the ultrasound images 1018. The image generator 1004 provides the ultrasound images 1018 to the image fuser 1006, the machine-learned model 1008, the processor system 1010, and the display device 1012.

The image fuser 1006 receives the ultrasound images 1018 from the image generator 1004 and also receives fuse instructions 1020. The fuse instructions 1020 can be received as a user input, or default register setting, and instruct the image fuser 1006 how to generate a fused image, such as by blending pixels, as a picture-in-picture, etc. From the superficial ultrasound image and the deep ultrasound image, and according to the fuse instructions 1020, the image fuser 1006 generates a fused ultrasound image 1022. The machine-learned model 806 is an example of the image fuser 1006, and the fused images 808-1, 808-2, 808-3, 808-4 are examples of the fused image generated by the image fuser 1006. The image fuser 1006 provides the fused image to the display device 1012.

The machine-learned model 1008 receives the ultrasound images 1018 from the image generator 1004 and can include any suitable number and type of machine-learned models implemented to generate any suitable type of inferences 1024 by processing the ultrasound images 1018. For example, the machine-learned model 1008 can generate interventional instrument data (e.g., needle data), including interventional instrument tracking data to track a tip of an interventional instrument, a depth of the interventional instrument tip in the ultrasound images, segmentations of the interventional instrument in the ultrasound images, etc. The machine-learned model 1008 can also generate an ROI for an ultrasound image, such as an ROI that includes an anatomy (e.g., an anatomy that the system determines is the target of an interventional instrument insertion), or an anatomy corresponding to a user selection (e.g., the user can select "vein" in a user interface and the machine-learned model 1008 can identify veins in the ROI, etc.). The machine-learned model 1008 can also generate a label, a bounding box, and/or a segmentation of an anatomy in an ultrasound image, such as an anatomy that the system determines is the target of an interventional instrument insertion, or an anatomy corresponding to a user selection (e.g., the user can select "vein" in a user interface and the machine-learned model 1008 can identify veins in the ultrasound images, etc.). The machine-learned model 1008 provides inferences 1024, including interventional instrument data, an ROI, and data representing an anatomy, to the processor system 1010.

The processor system 1010 receives the inferences 1024 (e.g., interventional instrument data, ROI, and data representing the anatomy) from the machine-learned model 1008, the ultrasound images 1018 from the image generator 1004, and user input 1026 (e.g., from a user interface displayed on the display device 1012). The user input 1026 can include user selections for how the user wants ultrasound images displayed, such as the selections enabled in the simultaneous-scanning panel 910. Based on the inferences 1024 from the machine-learned model 1008, the ultrasound images 1018 from the image generator 1004, and the user input 1026, the processor system 1010 generates the scan instructions 1014 to control the multi-array scanner 1002. For instance, the scan instructions 1014 can instruct the scanner 1002 to use a first transducer array to scan until an interventional instrument reaches a certain depth (e.g., a threshold depth) and then enable a second transducer array of the scanner 1002 once a tip of the interventional instrument passes the depth. The processor system 1010 also provides display instructions 1028 to the display device 1012. For example, the display instructions 1028 can be based on user input 1026 received via the simultaneous-scanning panel 910 that selects what ultrasound images to display on a user interface, such as to simultaneously display a superficial ultrasound image and a deep ultrasound image.

The display device 1012 receives the display instructions 1028 from the processor system 1010, the ultrasound images 1018 from the image generator 1004, and the fused ultrasound image 1022 from the image fuser 1006 and displays the ultrasound images according to the display instructions 1028. The image panel 916 is an example of ultrasound images displayed by the display device 1012 according to the display instructions 1028 received from the processor system 1010.

Example Device

Figure 11:
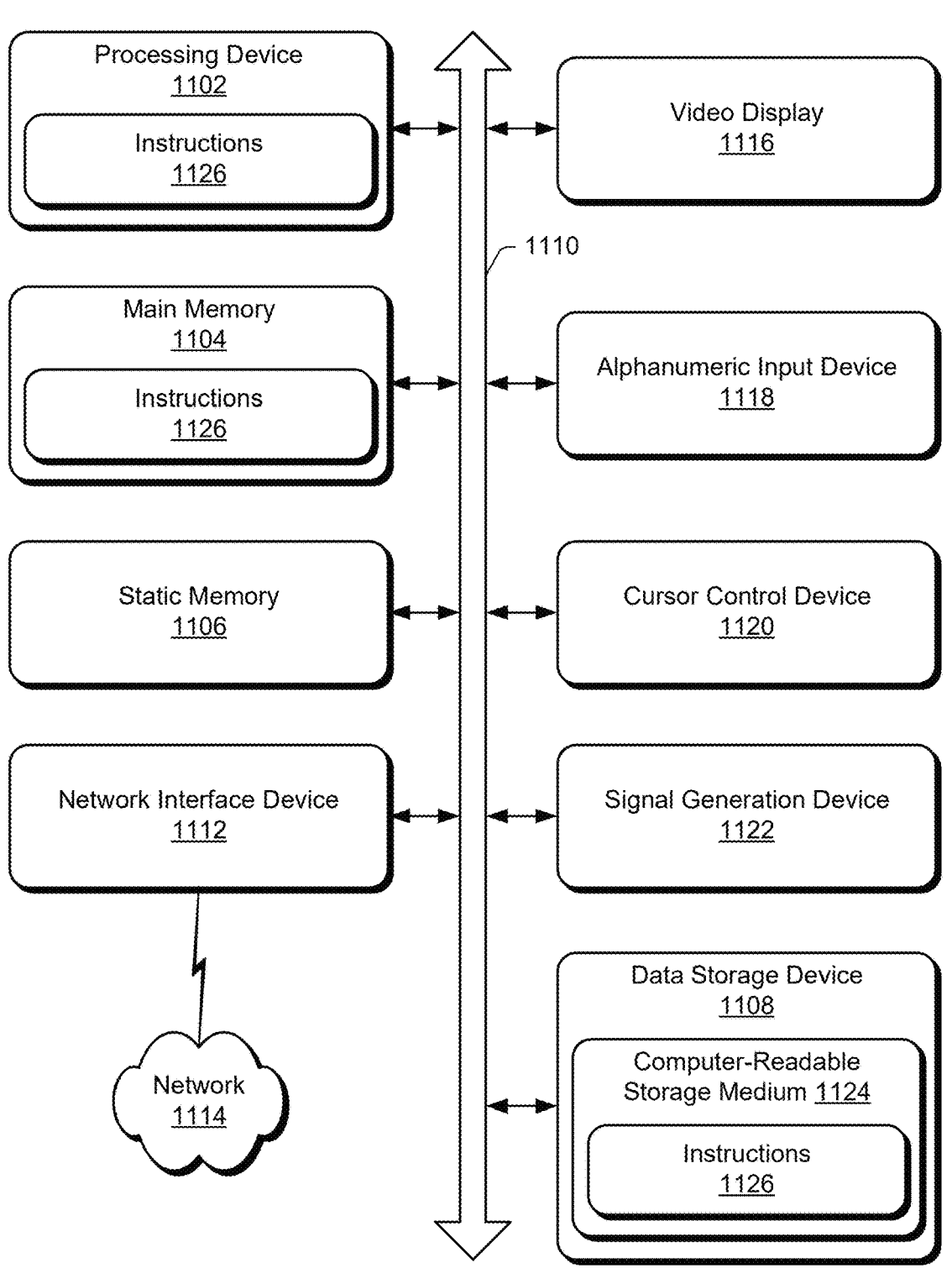
FIG. 11 illustrates an example device for managing an ultrasound system with simultaneous transducer arrays.

FIG. 11 illustrates a block diagram of an example computing device 1100 that can perform one or more of the operations described herein, in accordance with some implementations. The computing device 1100 can be connected to other computing devices in a local area network (LAN), an intranet, an extranet, and/or the Internet. The computing device 1100 can operate in the capacity of a server machine in a client-server network environment or in the capacity of a client in a peer-to-peer network environment. The computing device 1100 can be provided by a personal computer (PC), a server computer, a desktop computer, a laptop computer, a tablet computer, a smartphone, an ultrasound machine, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some implementations, the computing device 1100 is one or more of an ultrasound machine, an ultrasound scanner, an access point, a charging station, and a medical archiver.

The example computing device 1100 can include a processing device 1102 (e.g., a general-purpose processor, a programmable logic device (PLD), etc.), a main memory 1104 (e.g., synchronous DRAM, ROM, etc.), and a static memory 1106 (e.g., flash memory, a data storage device 1108, etc.), which can communicate with each other via a bus 1110. The processing device 1102 can be provided by one or more general-purpose processing devices such as a microprocessor, a central processing unit, or the like. In an illustrative example, the processing device 1102 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 1102 can also comprise one or more special-purpose processing devices such as an ASIC, an FPGA, a digital signal processor (DSP), a network processor, or the like. The processing device 1102 can be configured to execute the operations described herein, in accordance with one or more aspects of the present disclosure, for performing the operations and steps discussed herein.

The computing device 1100 can further include a network interface device 1112, which can communicate with a network 1114. The computing device 1100 also can include a video display unit 1116 (e.g., a liquid crystal display (LCD), an organic light-emitting diode (OLED), a cathode ray tube (CRT), etc.), an alphanumeric input device 1118 (e.g., a keyboard), a cursor control device 1120 (e.g., a mouse), and an acoustic signal generation device 1122 (e.g., a speaker, a microphone, etc.). In one embodiment, the video display unit 1116, the alphanumeric input device 1118, and the cursor control device 1120 can be combined into a single component or device (e.g., an LCD touch screen).

The data storage device 1108 can include a computer-readable storage medium 1124 on which can be stored one or more sets of instructions 1126 (e.g., instructions for carrying out the operations described herein, in accordance with one or more aspects of the present disclosure). The instructions 1126 can also reside, completely or at least partially, within the main memory 1104 and/or within the processing device 1102 during execution thereof by the computing device 1100, where the main memory 1104 and the processing device 1102 also constitute computer-readable media. The instructions 1126 can further be transmitted or received over the network 1114 via the network interface device 1112.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein are embodied in the data storage device 1108 of the computing device 1100 as executable instructions or code. Although represented as software implementations, the described modules can be implemented as any form of a control application, software application, signal processing and control module, hardware, or firmware installed on the computing device 1100.

While the computer-readable storage medium 1124 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

Example Machine-Learned Model

Many of the aspects described herein can be implemented using a machine-learned model. For the purposes of this disclosure, a machine-learned model is any model that accepts an input, analyzes, and/or processes the input based on an algorithm derived via machine-learning training, and provides an output. A machine-learned model can be conceptualized as a mathematical function of the following form:

$$f(\hat{s}, \theta) = \hat{y} \qquad \text{Equation (1)}$$

In Equation (1), the operator f represents the processing of the machine-learned model based on an input and providing an output. The term s represents a model input, such as ultrasound data. The model analyzes/processes the input s using parameters θ to generate output ŷ (e.g., object identification, object segmentation, object classification, etc.). Both § and § can be scalar values, matrices, vectors, or mathematical representations of phenomena such as categories, classifications, image characteristics, the images themselves, text, labels, or the like. The parameters θ can be any suitable mathematical operations, including but not limited to applications of weights and biases, filter coefficients, summations or other aggregations of data inputs, distribution parameters such as mean and variance in a Gaussian distribution, linear algebra-based operators, or other parameters, including combinations of different parameters, suitable to map data to a desired output.

Figure 12:
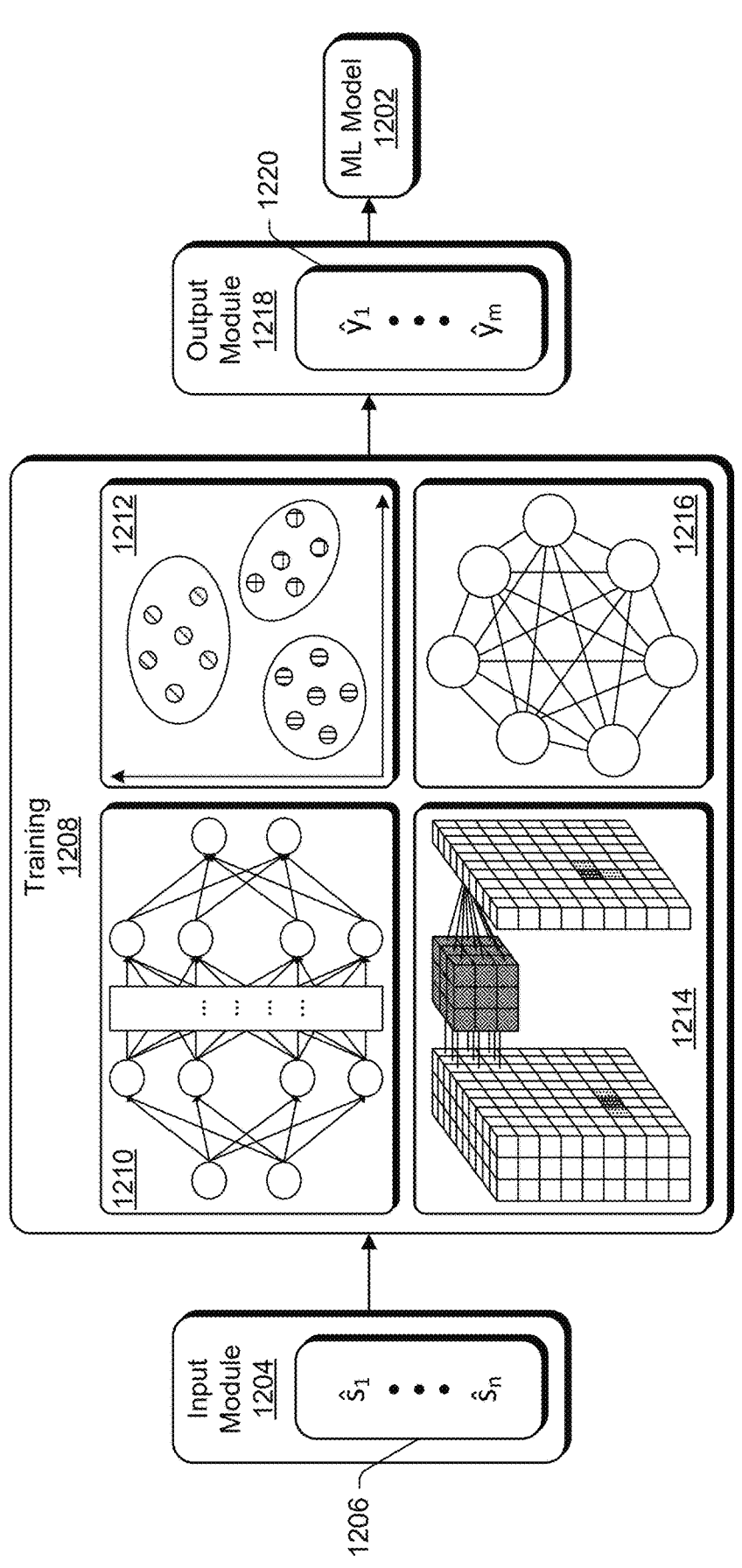
FIG. 12 represents an example machine-learning architecture used to train a machine-learned model M.

FIG. 12 represents an example machine-learning architecture 1200 used to train a machine-learned model M 1202. An input module 1204 accepts an input ŝ 1206, which can be an array with members $\hat{s}_1$ through $\hat{s}_n$. The input ŝ 1206 is fed into a training module 1208, which processes the input ŝ 1206 based on the machine-learning architecture 1200. For example, if the machine-learning architecture 1200 uses a multilayer perceptron (MLP) model 1210, the training module 1208 applies weights and biases to the input ŝ 1206 through one or more layers of perceptrons, each perceptron performing a fit using its own weights and biases according to its given functional form. MLP weights and biases can be adjusted so that they are optimized against a least mean square, logcosh, or other optimization function (e.g., loss function) known in the art. Although an MLP model 1210 is described here as an example, any suitable machine-learning technique can be employed, some examples of which include but are not limited to k-means clustering 1212, convolutional neural networks (CNN) 1214, a Boltzmann machine 1216, Gaussian mixture models (GMM), and long short-term memory (LSTM). The training module 1208 provides an input to an output module 1218. The output module 1218 analyzes the input from the training module 1208 and provides an output in the form of ŷ 1220, which can be an array with members $\hat{y}_1$ through $\hat{y}_m$. The output 1220 can represent a known correlation with the input s 1206, such as, for example, object identification, segmentation, and/or classification.

In some examples, the input ŝ 1206 can be a training input labeled with known output correlation values, and these known values can be used to optimize the output ŷ 1220 in training against the optimization/loss function. In other examples, the machine-learning architecture 1200 can categorize the output ŷ 1220 values without being given known correlation values to the inputs ŝ 1206. In some examples, the machine-learning architecture 1200 can be a combination of machine-learning architectures. By way of example, a first network can use the input ŝ 1206 and provide the output ŷ 1220 as an input SML to a second machine-learned architecture, with the second machine-learned architecture providing a final output $\hat{y}_f$. In another example, one or more machine-learning architectures can be implemented at various points throughout the training module 1208.

In some machine-learned models, all layers of the model are fully connected. For example, all perceptrons in an MLP model act on every member of ŝ. For an MLP model with a 100×100 pixel image as an input, each perceptron provides weights/biases for 10,000 inputs. With a large, densely layered model, this can result in slower processing and/or issues with vanishing and/or exploding gradients. A CNN, which can not be a fully connected model, can process the same image using 5×5 tiled regions, requiring only 25 perceptrons with shared weights, giving much greater efficiency than the fully connected MLP model.

Figure 13:
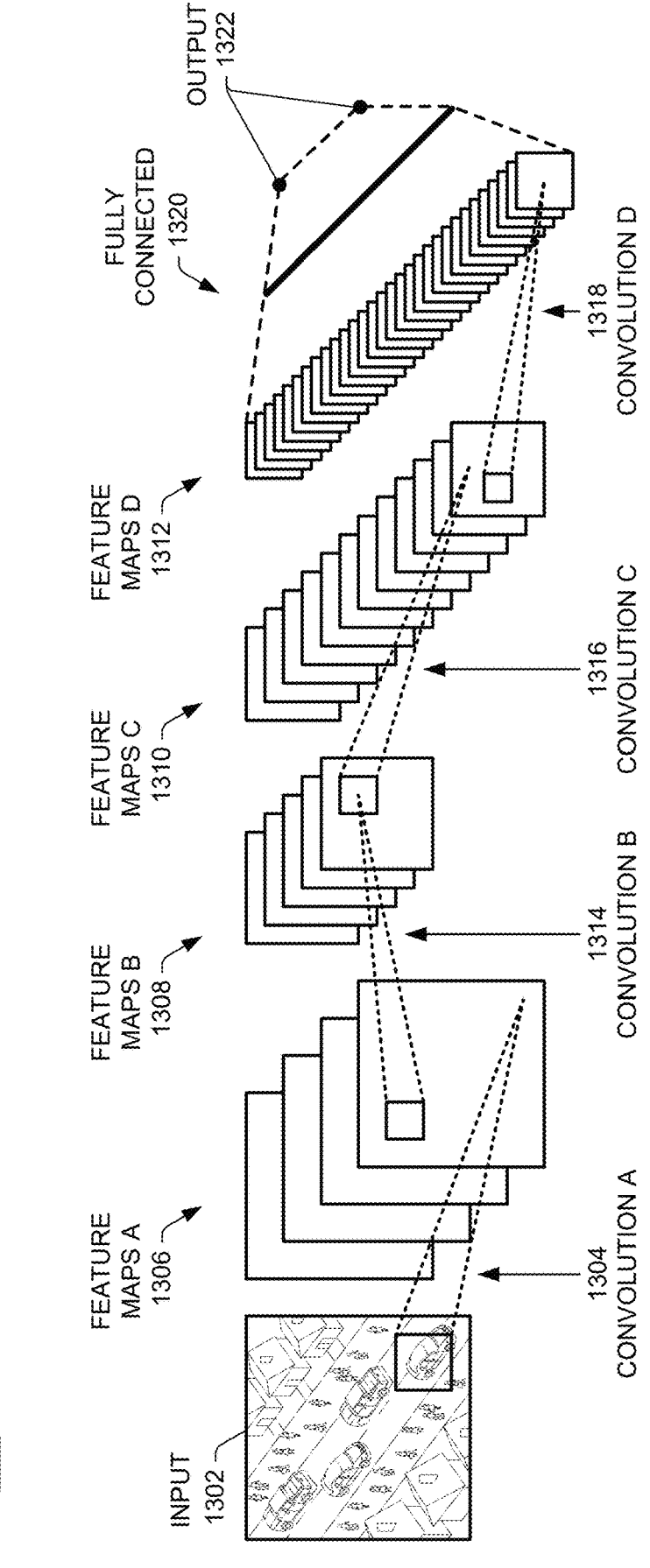
FIG. 13 represents an example model using a convolutional neural network (CNN) to process an input image, which includes representations of objects that can be identified via object recognition, such as people or cars.

FIG. 13 represents an example model 1300 using a CNN to process an input image 1302, which includes representations of objects that can be identified via object recognition, such as people or cars (or an anatomy, as described in relation to FIGS. 1-9). Convolution A 1304 can be performed to create a first set of feature maps (e.g., feature maps A 1306). A feature map can be a mapping of aspects of the input image 1302 given by a filter element of the CNN. This process can be repeated using feature maps A 1306 to generate further feature maps B 1308, feature maps C 1310, and feature maps D 1312 using convolution B 1314, convolution C 1316, and convolution D 1318, respectively. In this example, the feature maps D 1312 become an input for fully connected network layers 1320. In this way, the machine-learned model 1300 can be trained to recognize certain elements of the image, such as people, cars, or a particular patient anatomy, and provide an output 1322 that, for example, identifies the recognized elements. In some aspects, an inference generated with an ultrasound system can be appended to a feature map (e.g., feature map B 1308) generated by a neural network (e.g., CNN). In this way, a feature vector and/or inference can be used as a secondary/conditional input to the neural network.

Although the example of FIG. 13 shows a CNN as a part of a fully connected network, other architectures are possible and this example should not be seen as limiting. There can be more or fewer layers in the CNN. A CNN component for a model can be placed in a different order, or the model can contain additional components or models. There can be no fully connected components, such as a fully convolutional network. Additional aspects of the CNN, such as pooling, downsampling, upsampling, or other aspects known to people skilled in the art, can also be employed.

Example Methods

FIG. 14 depicts a method for a multi-array ultrasound scanner having simultaneous arrays. The method can be performed by an ultrasound device (e.g., ultrasound machine 102) or an ultrasound system (e.g., ultrasound system 100, ultrasound system 200, ultrasound system 500, ultrasound system 800-1, ultrasound system 800-2, ultrasound system 800-3, ultrasound system 1000). The method is shown as a set of blocks that specify operations performed but are not necessarily limited to the order or combinations shown for performing the operations by the respective blocks. Further, any one or more of the operations can be repeated, combined, reorganized, or linked to provide a wide array of additional and/or alternate methods. In portions of the following discussion, reference can be made to the example system 100 of FIG. 1 or to entities or processes as detailed in FIGS. 2-13, reference to which is made for example only. The techniques are not limited to performance by one entity or multiple entities operating on one device.

At 1402, first ultrasound data is generated based on reflections of first ultrasound signals transmitted by the first transducer array at an anatomy, the first ultrasound signals being focused at a first depth. For example, a first transducer array (e.g., first transducer array 504) transmits first ultrasound signals focused at a first depth. The first transducer array (e.g., first transducer array 504) receives reflections of the first ultrasound transducer signals transmitted at an anatomy and generates first ultrasound data.

At 1404, second ultrasound data is generated based on reflections of second ultrasound signals transmitted by the second transducer array at the anatomy, the second ultrasound signals being focused at a second depth that differs from the first depth. For example, a second transducer array (e.g., second transducer array 506) transmits second ultrasound signals focused at a second depth. The second transducer array (e.g., second transducer array 506) receives reflections of the second ultrasound transducer signals transmitted at the anatomy and generates second ultrasound data.

At 1406, a first image is generated, by one or more processors, based on the first ultrasound data. For example, a first image (e.g., first ultrasound image 510) is generated by one or more processors (e.g., processors 106) based on the first ultrasound data. Alternatively, an image processor (e.g., image generator 1004) can generate, alone or in combination with a processor (e.g., processors 106), the first image (e.g., first ultrasound image 510) based on the first ultrasound data. The first image can be a superficial image based on a first depth being approximately ten (10) centimeters of less.

At 1408, a second image is generated, by the one or more processors, based on the second ultrasound data. For example, a second image (e.g., second ultrasound image 512) is generated by one or more processors (e.g., processors 106) based on the second ultrasound data. Alternatively, an image processor (e.g., image generator 1004) can generate, alone or in combination with a processor (e.g., processors 106), the second image (e.g., second ultrasound image 512) based on the second ultrasound data. The second image can be a deep image based on a second depth being approximately thirty (30) centimeters or less. The display can be configured to display controls to modify an operation for at least the first transducer array or the second transducer array response to a touch input via the display.

At 1410, the first image and the second image are displayed on a display. For example, an ultrasound image (e.g., ultrasound image 118) is displayed on a display (e.g., display device 108). One or more processors can be configured to cause the display to display the first image and the second image simultaneously in real time. As yet another example, the first image (e.g., first ultrasound image 510) and the second image (e.g., second ultrasound image 512) can be displayed on a user interface (e.g., user interface 508) on a display (e.g., display device 108). In one aspect, the display can be configured to display a fused image that includes at least a first portion of the second image being overlaid on at least a second portion of the first image. The ultrasound device can include an image fuser and an image generator. The image generator can be configured, in combination with one or more processors, to generate the first image and the second image. The image fuser can be configured to generate the fused image based on fuse instructions and instructions from the image generator.

At 1412, the first image can be automatically replaced with the second image when an interventional instrument, detected within the first ultrasound data and displayed within the first image, reaches a region of interest or a threshold depth of the first image. For example, the first image (e.g., first ultrasound image 604) can be automatically replaced (e.g., indicated by the arrow 610 of FIG. 6) with the second image (e.g., second ultrasound image 612) when an interventional instrument (e.g., interventional instrument 606) reaches an ROI (e.g., area 708 of an ROI) or a threshold depth (e.g., threshold depth 608). In one aspect, one or more processors can be configured to automatically replace the first image with the second image on the display when an interventional instrument, detected within the first ultrasound sound data and displayed within the first image, reaches a threshold depth on the first image.

In another aspect, the one or more processors can be configured to cause the first transducer array to transmit the first ultrasound signals, the first image including an interventional instrument detected within the first ultrasound data as the interventional instrument is inserted into a subject toward a threshold depth. As the interventional instrument is inserted toward the threshold depth, the first ultrasound data is generated and the first image is displayed on the display. Upon the interventional instrument reaching the threshold depth, the second ultrasound data is generated, the second image is displayed on the display, and the first image can cease to be displayed on the display. The one or more processors can be configured to cease generation of the first ultrasound data upon the interventional instrument reaching the threshold depth.

In one aspect, the one or more processors can be configured to cause a region of interest to be indicated on the display, the region of interest being determined based on a user input. The user input can be a depth and the region of interest can be determined by a machine-learned model based on the depth. The first transducer array can be a linear transducer array and the second transducer array can be a phased transducer array. In another aspect, the first transducer array can be a linear transducer array or a phased transducer array and the second transducer array can be a doppler transducer array or a color-transducer array.

In one aspect, the multi-array ultrasound scanner can include one or more sensors configured to generate a trigger signal. The one or more sensors can be configured to generate the trigger signal based on pressure, touch, or orientation of the multi-array ultrasound scanner. The trigger can cause the first transducer array to transmit first ultrasound signals, the second transducer array to transmit second ultrasound signals, or the first transducer array to transmit first ultrasound signals and the second transducer array to transmit second ultrasound signals.

The trigger signal can enable an examination preset that determines a respective operation mode for the first transducer array and the second transducer array. The trigger signal can enable first steps of a protocol for the first transducer array and second steps of the protocol for the second transducer array. The trigger signals can enable a machine-learned model that identifies a target for an interventional instrument detected within the first ultrasound data. The trigger signal can enable a threshold depth wherein the ultrasound device transitions from the first transducer array to the second transducer array when an interventional instrument detected within the first ultrasound data reaches the threshold depth or the ultrasound device can automatically replace the first image with the second image when the interventional instrument detected within the first ultrasound data reaches the threshold depth.

For the methods described herein and the associated flow chart(s) and flow diagram(s), the orders in which operations are shown and/or described are not intended to be construed as a limitation. Instead, any number or combination of the described method operations can be combined in any order to implement a given method or an alternative method, including by combining operations from the flow chart or diagram and the earlier-described schemes and techniques into one or more methods. Operations can also be omitted from or added to the described methods. Further, described operations can be implemented in fully or partially overlapping manners.

CONCLUSION

Embodiments of ultrasound with simultaneous transducer arrays as described herein are advantageous, as they provide less examination scanning time for a patient, provide automatic switching of ultrasound images without user intervention when an interventional instrument reaches a threshold depth, provide multiple ultrasound images viewed on substantially the same plane, and other benefits. The techniques of ultrasound with simultaneous transducer arrays disclosed herein also enable individual control of the transducer arrays of an ultrasound system. The ultrasound with simultaneous transducer arrays provides increased scanning efficiency, improved patient experience, and similar benefits.

While the present subject matter has been described in detail with respect to various specific example implementations thereof, each example is provided by way of explanation and not limitation of the disclosure. Those skilled in the art, upon attaining an understanding of the foregoing, can readily produce alterations to, variations of, and equivalents to such implementations. Accordingly, the subject disclosure does not preclude inclusion of such modifications, variations, and/or additions to the present subject matter as would be readily apparent to one of ordinary skill in the art. For instance, features illustrated or described as part of one implementation can be used with another implementation to yield a still further implementation. Thus, it is intended that the present disclosure covers such alterations, variations, and equivalents.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (a-a, a-a-a, a-a-b, a-a-c, a-b-b, a-c-c, b-b, b-b-b, b-b-c, c-c, and c-c-c or any other ordering of a, b, and c).

While various embodiments of the disclosure are described in the foregoing description and shown in the drawings, it is to be distinctly understood that this disclosure is not limited thereto but can be variously embodied to practice within the scope of the following claims. From the foregoing description, it will be apparent that various changes can be made without departing from the spirit and scope of the disclosure as defined by the following claims.

What is claimed is:

1. An ultrasound device comprising:
a multi-array ultrasound scanner configured to generate ultrasound data based on reflections of ultrasound signals transmitted by the multi-array ultrasound scanner at an anatomy, the multi-array ultrasound scanner including:
one or more sensors configured to generate a trigger signal based on pressure, touch, or orientation of the multi-array ultrasound scanner, the trigger signal enabling a threshold depth to be used by the ultrasound device; and
at least a first transducer array and a second transducer array, the multi-array ultrasound scanner configured to:
generate first ultrasound data based on reflections of first ultrasound signals transmitted by the first transducer array at the anatomy, the first ultrasound signals focused at a first depth; and
generate second ultrasound data based on reflections of second ultrasound signals transmitted by the second transducer array at the anatomy, the second ultrasound signals focused at a second depth, the second depth differing from the first depth;
a display device configured to display one or more images; and
one or more processors, the one or more processors configured to generate a first image based on the first ultrasound data and generate a second image based on the second ultrasound data, each of the first image and the second image displayable via the display device, the one or more processors configured to cause the ultrasound device to:
transition from the first transducer array to the second transducer array when an interventional instrument detected within the first ultrasound data reaches the threshold depth; or
replace the first image on the display device with the second image when the interventional instrument detected within the first ultrasound data reaches the threshold depth.

2. The ultrasound device of claim 1, wherein:
the first image comprises a superficial image based on the first depth being approximately ten (10) centimeters or less; and
the second image comprises a deep image based on the second depth being approximately thirty (30) centimeters or less.

3. The ultrasound device of claim 1, wherein the one or more processors are configured to:
cause the first transducer array to transmit the first ultrasound signals, the first image including the interventional instrument detected within the first ultrasound data as the interventional instrument is inserted into a subject toward the threshold depth;
wherein:
as the interventional instrument is inserted toward the threshold depth the first ultrasound data is generated and the first image is displayed on the display device; and
upon the interventional instrument reaching the threshold depth the second ultrasound data is generated, the second image is displayed on the display device, and the first image ceases to be displayed on the display device.

4. The ultrasound device of claim 3, wherein the one or more processors are configured to cease generation of the first ultrasound data upon the interventional instrument reaching the threshold depth.

5. The ultrasound device of claim 1, wherein the one or more processors are configured to:
cause a region of interest to be indicated in the first image displayed on the display device, the region of interest determined based on a user input.

6. The ultrasound device of claim 5, wherein the user input is a depth and the region of interest is determined by a machine-learned model based on the depth.

7. The ultrasound device of claim 1, wherein:
the first transducer array comprises a linear transducer array; and
the second transducer array comprises a phased transducer array.

8. The ultrasound device of claim 1, wherein:
the first transducer array comprises a linear transducer array or a phased transducer array; and
the second transducer array comprises a doppler transducer array or a color-transducer array.

9. The ultrasound device of claim 1, wherein:

the display device is configured to display a fused image, the fused image comprising at least a first portion of the second image being overlaid on at least a second portion of the first image.

10. The ultrasound device of claim 9, further comprising:

an image fuser; and an image generator, the image generator, in combination with the one or more processors, generating the first image and the second image;

wherein the image fuser generates the fused image based on fuse instructions and instructions from the image generator.

11. A method for a multi-array ultrasound scanner having a first transducer array and a second transducer array, the method comprising:

generating, by one or more sensors, a trigger signal based on pressure, touch, or orientation of the multi-array ultrasound scanner, the trigger signal enabling a threshold depth to be used by the multi-array ultrasound scanner;

generating first ultrasound data based on reflections of first ultrasound signals transmitted by the first transducer array at an anatomy, the first ultrasound signals being focused at a first depth;

generating second ultrasound data based on reflections of second ultrasound signals transmitted by the second transducer array at the anatomy, the second ultrasound signals being focused at a second depth, the second depth differing from the first depth;

generating, by one or more processors, a first image based on the first ultrasound data;

generating, by the one or more processors, a second image based on the second ultrasound data;

displaying, on a display device, the first image; and displaying the second image on the display device by, the displaying of the second image including:

causing the multi-array ultrasound scanner to transition from the first transducer array to the second transducer array when an interventional instrument, detected within the first ultrasound data and displayed within the first image, reaches the threshold depth; or automatically replacing the first image with the second image when the interventional instrument, detected within the first ultrasound data and displayed within the first image, reaches the threshold depth.

12. An ultrasound system comprising:

a multi-array ultrasound scanner configured to generate ultrasound data based on reflections of ultrasound signals transmitted by the multi-array ultrasound scanner at an anatomy, the multi-array ultrasound scanner having:

at least a first transducer array and a second transducer array, the multi-array ultrasound scanner configured to:

generate first ultrasound data based on reflections of first ultrasound signals transmitted by the first transducer array at the anatomy, the first ultrasound signals focused at a first depth; and generate second ultrasound data based on reflections of second ultrasound signals transmitted by the second transducer array at the anatomy, the second ultrasound signals focused at a second depth, the second depth differing from the first depth; and one or more sensors configured to generate a trigger signal based on pressure, touch, or orientation of the multi-array ultrasound scanner, the trigger signal configured to trigger initiation of:

an examination preset, the examination preset configured to determine a respective operational mode for the first transducer array and the second transducer array;

first steps of a protocol for the first transducer array and second steps of the protocol for the second transducer array; or a machine-learned model that identifies a target for an interventional instrument detected within the first ultrasound data; and one or more processors, the one or more processors configured to:

generate a first image based on the first ultrasound data; and generate a second image based on the second ultrasound data; and a display device configured to display the first image and the second image.

13. The ultrasound system of claim 12, wherein the display device is configured to display controls to modify an operation for at least the first transducer array or the second transducer array responsive to a touch input via the display device.

14. The ultrasound system of claim 12, wherein:

the first image includes a superficial image based on the first depth being approximately ten (10) centimeters or less; and the second image includes a deep image based on the second depth being approximately thirty (30) centimeters or less.

15. The ultrasound system of claim 12, wherein the one or more processors are configured to, responsive to the interventional instrument reaching a threshold depth or a region of interest, generate the second image and cease generation of the first ultrasound data.

16. The ultrasound system of claim 12, wherein the one or more processors are configured to cause a region of interest to be indicated on the first image, the region of interest determined based on a user input.

17. The ultrasound system of claim 16, wherein the user input is a depth and the region of interest is determined by a machine-learned model based on the depth.

18. The ultrasound system of claim 12, wherein:

the first transducer array comprises a linear transducer array; and the second transducer array comprises a phased transducer array.

19. The ultrasound system of claim 12, wherein:

the first transducer array comprises a linear transducer array or a phased transducer array; and the second transducer array comprises a doppler transducer array or a color-transducer array.

20. The method of claim 11, further comprising:

determining, by a machine-learned model and based on a depth defined by a user input, a region of interest in the first image; and displaying an indication of the region of interest in the first image via the display device.

* * * * *